(12) United States Patent
Krishna et al.

(10) Patent No.: US 8,739,604 B2
(45) Date of Patent: Jun. 3, 2014

(54) GAS SENSOR AND METHOD OF MAKING

(75) Inventors: Kalaga Murali Krishna, Bangalore (IN); Geetha Karavoor, Kerala (IN); John Patrick Lemmon, Schoharie, NY (US); Jun Cui, Glenville, NY (US); Vinayak Tilak, Niskayuna, NY (US); Mohandas Nayak, Karnataka (IN); Ravikumar Hanumantha, Karnataka (IN)

(73) Assignee: Amphenol Thermometrics, Inc., St. Marys, PA (US)

( * ) Notice: Subject to any disclaimer, the term of this patent is extended or adjusted under 35 U.S.C. 154(b) by 1929 days.

(21) Appl. No.: 11/960,781

(22) Filed: Dec. 20, 2007

(65) Prior Publication Data

US 2009/0159445 A1 Jun. 25, 2009

(51) Int. Cl.
*G01N 27/00* (2006.01)

(52) U.S. Cl.
USPC .......... 73/31.06; 73/23.2; 73/31.05; 257/414; 422/50; 422/83; 422/88; 422/90; 422/98; 438/48; 438/49

(58) Field of Classification Search
USPC ................ 73/23.2, 23.3, 23.31, 23.34, 31.05, 73/31.06; 257/414; 422/50, 83, 84, 90, 97; 438/48, 49, 108
See application file for complete search history.

(56) References Cited

U.S. PATENT DOCUMENTS

| | | | |
|---|---|---|---|
| 4,840,913 A | 6/1989 | Logothetis et al. | |
| 5,486,336 A | 1/1996 | Dalla Betta et al. | |
| 5,877,406 A | 3/1999 | Kato | |
| 6,656,872 B2 | 12/2003 | Labhasetwar et al. | |
| 6,698,283 B2 * | 3/2004 | Wado et al. | 73/204.26 |
| 7,017,389 B2 | 3/2006 | Gouma | |
| 2005/0097941 A1 | 5/2005 | Sandvik et al. | |
| 2005/0235735 A1 | 10/2005 | Doll et al. | |
| 2006/0064029 A1 | 3/2006 | Arad | |
| 2006/0091022 A1 | 5/2006 | Ruud et al. | |
| 2006/0267051 A1 | 11/2006 | Gstrein et al. | |
| 2007/0199819 A1 | 8/2007 | Ito | |

FOREIGN PATENT DOCUMENTS

JP 10054817 A 2/1998
JP 2007263582 3/2006

OTHER PUBLICATIONS

Imawan et al., Gas-sensing characteristics of modified-MoO3 thin films using Ti-overlayers for NH3 gas sensors, Sensors and Actuators B 64 (2000) pp. 193-197.*
Angana Sen, Panchanan Pramanik, A chemical synthetic route for the preparation of fine-grained metal tungstate powders (M=Ca, Co, Ni, Cu, Zn), Journal of the European Ceramic Society, vol. 21, Issue 6, Jun. 2001, pp. 745-750.*
Jimenez, I.; Vila, A.M.; Calveras, A.C.; Morante, J.R.;, "Gas-sensing properties of catalytically modified WO3 with copper and vanadium for NH3 detection," Sensors Journal, IEEE , vol. 5, No. 3, pp. 385-391, Jun. 2005.*

(Continued)

*Primary Examiner* — Paul Hyun
*Assistant Examiner* — Robert Eom
(74) *Attorney, Agent, or Firm* — Blank Rome LLP

(57) ABSTRACT

A gas sensor is disclosed. The gas sensor includes a gas sensing layer, at least one electrode, an adhesion layer, and a response modification layer adjacent to said gas sensing layer and said layer of adhesion. A system having an exhaust system and a gas sensor is also disclosed. A method of fabricating the gas sensor is also disclosed.

2 Claims, 12 Drawing Sheets

(56) References Cited

OTHER PUBLICATIONS

Kim, Yong Shin, Microheater-integrated single gas sensor array chip fabricated on flexible poyimide substrate, Sensors and Actuators B 114 (2006) 410-417.*

Meixner et al., Metal oxide sensors, Sensors and Actuators B 33 (1996) 198-202.*

GB Search Report—Apr. 14, 2009, Application No. GB0822498.2.

Ando et al.; "Optical and Electrical H2- and NO2-Sensing Properties of Au / InxOyNz Films"; IEEE Sensors Journal, vol. 04, No. 2, Apr. 2004; 232-236.

M. Blo et al.; "Synthesis of pure and loaded powders of WO3 for NO2 detection through thick film technology"; Sensors and Actuators B 103 (2004) 213-218.

* cited by examiner

GAS SENSOR AND METHOD OF MAKING

BACKGROUND

The invention relates generally to the area of gas sensing. More specifically, the invention relates to the sensing of $NO_x$ gas.

Environmental considerations are the primary motivating factors to develop $NO_x$ sensors. $NO_x$ emissions react with gases such as SOx, CO and moisture (water vapor) in the air to produce smog and acid rain. One of the major sources of $NO_x$ emissions is internal combustion engine exhaust.

The European Euro VI emission standards for light commercial vehicles (category N1-I, N1-II and N1-III), to be implemented by September 2015, require $NO_x$ emission levels below 0.5 gm/hp-hr. This typically translates to less than 50 ppm of $NO_x$ tail pipe emissions. Development of cost-effective sensors that can give reliable readout at such low concentration levels of analyte, and which can deliver robust performance even in harsh environments, is one of the major challenges facing present day emissions monitoring technology.

The current paradigm in improving the efficiency of internal combustion engines utilizes the technology of lean burn, whereby very high air:fuel ratios ($\sim 10^2$:1), as compared to conventional stoichiometric ratio (typically ~20:1), are used. While the lean burn technology improves the efficiency of the engine, it also results in higher $NO_x$ emissions.

Any emissions control scheme that adversely impacts or limits efficiency will not be commercially viable. This necessitates real time monitoring of $NO_x$ emission levels and use of this information to dynamically control engine operating parameters (such as compression ratio, etc.) and exhaust after-treatment systems (such as catalytic filters, etc.) to achieve optimal engine efficiency and optimal emissions control, respectively.

One of current $NO_x$ gas sensing technology in the market employs yttria stabilized zirconia (YSZ) based sensors. The sensors are essentially a multi-chamber electrochemical cell measuring the oxygen changes as a result of $NO_x$ decomposition. Such technology requires catalysts such as platinum (Pt). However, the performance of the catalyst degrades upon exposure to $SO_x$ and water vapor, commonly present in the exhaust from internal combustion engine. This is one of the factors contributing to lowering the working life of such sensors. Further, the relatively intricate design of such sensors makes them expensive to replace on a regular basis.

Another current gas sensing technology in the market employs semiconductor sensors. As with any technology, this technology presents situation specific disadvantages and advantages. For example, gas emissions monitoring applications often require quantitative estimation of a particular or few gas species (e.g., $NO_x$) in a multiple gas species environment. Such semiconductor sensors, however, are sensitive to a broad range of gases, and therefore are of limited utility in such $NO_x$ gas sensing applications. Furthermore, these sensors are prone to long term instability because of their polycrystalline nature. On the other hand, this technology has the advantages of being solid-state, such as rigid construction and compact size. Further, the technology is amenable to readout using simple electronics, thereby reducing cost of system manufacture, operation, maintenance and replacement. In addition, semiconductor sensors allow a wide range of response tunability via introduction of suitable dopants, control of morphology of gas sensing surface, control of gas sensor operating parameters, amongst other controllable factors.

A gas sensor that is semiconductor based, can make quantitative estimation of $NO_x$ gas even at low concentration levels, and has a long working life, would, therefore, be highly desirable.

BRIEF DESCRIPTION

Embodiments of the invention are directed towards a gas sensor and a method for making the gas sensor.

In accordance with one exemplary embodiment of the invention, a gas sensor is disclosed. The gas sensor includes a gas sensing layer, at least one electrode, an adhesion layer, and a response modification layer adjacent to said gas sensing layer and said layer of adhesion.

In accordance with one exemplary embodiment of the invention, a system including a system for gas sensing is provided. The system includes an exhaust system to transport gases, and a gas sensor. The gas sensor includes a gas sensing layer, at least one electrode, an adhesion layer, and a response modification layer adjacent to said gas sensing layer and said layer of adhesion.

In accordance with one exemplary embodiment of the invention, a method for making a gas sensor is provided. The method includes disposing a heating layer, disposing a first glass layer adjacent to the heating layer, disposing a temperature sensing layer adjacent to the first glass layer, disposing a second glass layer adjacent to the temperature sensing layer, disposing at least one electrode adjacent to the second glass layer, disposing an adhesion layer adjacent to the at least one electrode, disposing a response modification layer adjacent to the adhesion layer, and disposing a gas sensing layer adjacent to the response modification layer.

In accordance with one exemplary embodiment of the invention, a gas sensor is disclosed. The gas sensor includes a gas sensing layer including at least one metal oxide compound and at least two dopant species, wherein the metal is a chemical element selected from the group consisting of W, Ta, and Nb, and wherein the dopant species is a chemical element selected from the group consisting of Re, Ni, V, Ta, Nb, Mo, and Zr. The gas sensing layer is capable to detecting at least one analyte selected from the group NO, $NO_2$, $NH_3$, $H_2O$, and combinations thereof in harsh environments. The gas sensor includes at least one electrode in communication with said sensing layer, an adhesion layer including a chemical element selected from the group consisting of Ti, Cr, and combinations thereof, and a response modification layer including at least one chemical element selected from the list Ti, Re, Ni, Ta, Nb, Mo, Zr, and combinations thereof. The response modification layer is adjacent to said gas sensing layer and said layer of adhesion.

These and other advantages and features will be more readily understood from the following detailed description of preferred embodiments of the invention that is provided in connection with the accompanying drawings.

DRAWINGS

DETAILED DESCRIPTION

Figure 1:
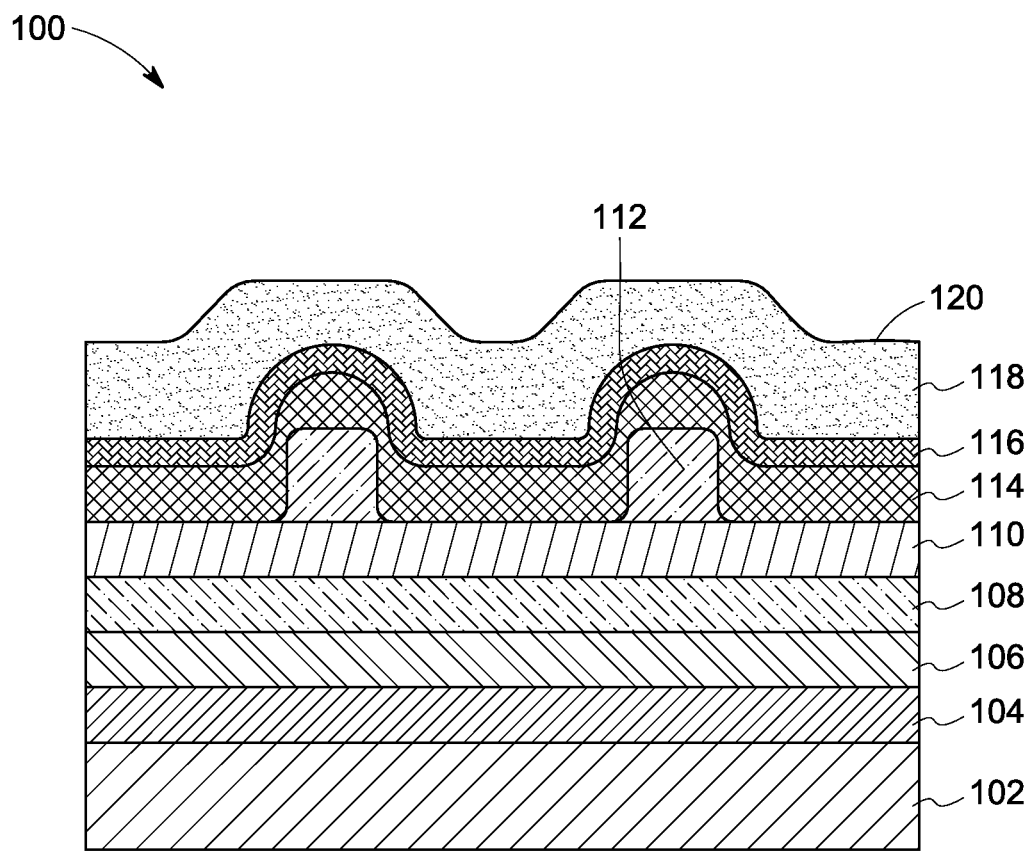
FIG. 1 is a diagrammatical representation of a cross-sectional view of a $NO_x$ gas sensor in accordance with an exemplary embodiment of the invention.

In the following description, whenever a particular aspect or feature of the invention is said to comprise or consist of at least one element of a group and combinations thereof, it is understood that the aspect or feature may comprise or consist of any of the elements of the group, either individually or in combination with any of the other elements of that group.

In the following specification and the claims that follow, the singular forms "a", "an" and "the" include plural referents unless the context clearly dictates otherwise.

A gas sensor may be used to determine if an "analyte" is present and/or to quantify an amount of the analyte. As used herein, the term "analyte" may refer to any substance to be detected and/or quantified, including but not limited to a gas, a vapor, a bioanalyte, particulate matter, and a combination thereof.

Since the primary constituents of $NO_x$, i.e., NO and $NO_2$ are interconvertible, reliable estimation of total $NO_x$ may be achieved if the response of the gas sensor, i.e., the $NO_x$ concentration dependent change in resistance of the gas sensor is equal (in terms of magnitude and sign) for both NO and $NO_2$. Thus, if $\Delta R(NO_2, c)$ and $\Delta R(NO, c)$ be the response of the sensor to concentration "c" of $NO_2$ and NO respectively, then a response ratio "rr" (defined below) close to unity would be desirable.

$$rr = \Delta R(NO_2, c)/\Delta R(NO, c) \qquad (1)$$

As used herein, the term "equisensitivity" refers to "rr" defined according to equation (1) when it is in a range from about 0.5 to about 3.

As used herein, the term "adjacent," when used in context of discussion of different components comprising the gas sensor refers to "immediately next to" or it refers to the situation wherein other components present between the components under discussion.

As used herein, the term "communication," when used in context of discussion of more than one component comprising the gas sensor may mean that any change in an electrical characteristic of one component is reflected at, and therefore, detectable and measurable via, the other component.

As used herein, the term "self-consistent," when used in the context of discussion of the chemical formula of a chemical compound composing a host component of a gas sensing layer of a gas sensor may mean that the said chemical formula is consistent with established scientific principles that would be known to one skilled in the art. Necessarily implied in the said definition of the term "self-consistent" is the situation wherein the said chemical formula represents a metal oxide inorganic compound. In other words, the said chemical formula must represent an inorganic metal oxide chemical composition. A general example of chemical formula of host component of the gas sensor may be $Ta_2O_5$, $WO_{2.9}$.

As used herein, the term "thin film," when used in the context of discussion of the gas sensing layer of a gas sensor refers to the situation wherein the thickness of the said gas sensing layer is from about 10 nm to about 500 nm.

As used herein, the term "thick film," when used in the context of discussion of the gas sensing layer of a gas sensor refers to the situation wherein the thickness of the said gas sensing layer is from about 500 nm to about 500 μm.

As used herein, the term "pellet", when used in the context of discussion of the gas sensing layer of a gas sensor refers to the situation wherein the thickness of the said gas sensing layer is from about 500 μm to about 3 mm.

As used herein, the term "neutral", when used in the context of discussion of the host component of a gas sensing layer and a one or more dopant species present in the host component of the said gas sensing layer refers to the situation wherein the oxidation state of the dopant species when present in the host component of the gas sensing layer is such that the said dopant is neither p-type nor n-type.

As used herein, the term "platform", when used in the context of discussion of a gas sensing layer of a gas sensor, refers to some or all of the components of the gas sensor other than the gas sensing layer itself.

As used herein, the term "harsh environment" or "harsh environments" refers to an environment within a volume that is in the vicinity of the gas sensing layer, and in which are present the analytes whose detection and/or estimation is being sought. The temperature within this volume may not be uniform, i.e., the temperature at/of different locations within this volume can be different, and can be from about 200° C. to about 800° C. Present at different locations within this volume can be different amounts of corrosive chemical species including but not limited to $NO_x$, $SO_x$, $H_2O$, particulate matter, hydrocarbons, and a combination thereof.

As used herein, the term "response modification layer" refers to a layer which serves to introduce dopants into a gas sensing layer via surface doping through the mechanism of diffusion. This surface doping may result in a modification of the response of the gas sensing layer for a given set of operating parameters and/or operating environments.

As used herein, the term "glass" refers to any suitable material that may be used to form a separating layer, that in a given embodiment of the gas sensor, has sufficient thermal conductivity to provide a sufficiently large heat link between the elements that the separating layer segregates, and which has sufficient electrical resistivity to provide sufficient electrical resistance between the elements that the separating layer segregates.

A gas sensor can be any device capable of producing an electrical signal proportional to a response characteristic that can be modulated upon exposure to gases. Examples of suitable devices include, but are not limited to, a resistor, a field effect transistor, a capacitor, a diode, and a combination thereof.

Examples of suitable gases to be sensed include, but are not limited to, NO, $NO_2$, $SO_x$, $O_2$, $H_2O$, $NH_3$, CO, and combinations thereof. In one embodiment, the gas sensor may not be susceptible to poisoning by $SO_2$ and $CO_2$ gases.

Referring to the drawings in general and to FIG. 1 in particular, it will be understood that the illustrations are for the purpose of describing a preferred embodiment of the invention and are not intended to limit the invention thereto.

FIG. 1 is a diagrammatical representation of one embodiment of a gas sensor 100 that may be used to detect an analyte. Although, $NO_x$ is used as an example with respect to some of the embodiments described, note that the gas sensor may be useful to detect other analytes, such as, for example, $O_2$, $H_2O$, CO, $SO_x$, $NH_3$, and combinations thereof. The gas sensor 100 might be, for example, an in-situ gas sensor that directly samples a gas stream to be analyzed. In this way, the gas sensor 100 can be exposed to the gas stream and generate a detection signal indicating whether a particular analyte (e.g., $NO_x$) is present. The gas sensor 100 can also generate a signal proportional to the concentration of the analyte and thereby measure the concentration of the analyte.

The illustrated embodiment 100 includes a substrate 102. On this substrate layer is disposed a heater 104. A first glass layer 106 is positioned above the heater 104. On the first glass layer 106 is disposed a temperature sensing layer 108. A second glass layer 110 is positioned above the temperature sensing layer 108. On the second glass layer 110 is disposed at least one electrode 112. An adhesion layer 114 completely covers the at least one electrode 112, and also is in contact with the second glass layer 110. A response modification layer 116 is disposed onto the adhesion layer 114. Upon this response modification layer 116 is disposed a gas sensing layer 118 which has a gas sensing surface 120. In some embodiments, the gas sensor 100 may include an element for heating the gas sensor. In one embodiment, an element for heating the gas sensor 100 may be disposed adjacent to the gas sensing layer 118, or it may be embedded within the gas sensing layer, or adjacent to the substrate layer 102, or on the packaging and any combinations thereof, and/or be covered with an electrically insulating and thermally conducting layer. The heater 104 may be an element that is separate from the main gas sensor 100, such as a metal (e.g., Pt) layer disposed adjacent to the gas sensing layer 118. The heater 104 may also be the gas sensing layer 118 itself. In one non-limiting example, a large current may be passed through the gas sensing layer in order to heat it to a desired temperature. The addition of heat, to the surface 120 of the gas sensing layer 118 also may result in faster response and recovery times. Not to be limited by any particular theory, it is believed that the heat decreases the resident time of each gas species at the surface 120 of the gas sensing layer 118. The heater 104 may also allow for adjusting the temperature of the gas sensor 100 to allow for higher sensitivity to gas species that are predisposed to superior detection at higher temperature ranges even when the gas stream environment to be measured has not reached such temperatures. This may be important in such applications that require gas sensing when an engine has only recently been started. Keeping the gas sensor 100 at a constant temperature, such as the maximum operable temperature, also can be used to ignore any dependence of the response signal on temperature, thus, allowing for simpler interpretation of the response signal. Additionally, the heating of the gas sensor 100 may be intentionally modified to provide a selective response to a variety of gases as driven by the temperature dependent selectivity and/or sensitivity of the gas sensing layer 118 to one or more species of analyte. Selectivity as used herein, refers to the ability of a gas sensor to discriminate between different presented analyte species. Sensitivity as used herein, refers to the ability of a gas sensor to display a change in an electrical characteristic when an analyte is presented to it. Selectivity, therefore, may be due to differing sensitivities towards different analyte species.

In one embodiment, the gas sensing layer 118, may in the form of a thin film. In another embodiment, the gas sensing layer 118, may be in the form of a thick film. In yet another embodiment, the gas sensing layer 118, may be in the form of a pellet.

In one embodiment, a catalyst layer may be disposed adjacent to the gas sensing layer. Such a catalyst layer may aid in the chemical conversion of one or more analyte species, into one or more analyte species which are amenable to detection by the said gas sensing layer. Suitable materials from which said catalyst layer may be composed include, but are not limited to, Pt, $RuO_2$, and combinations thereof.

In one embodiment, the substrate 102 shown in FIG. 1 may be composed of alumina. In another embodiment, the substrate 102 shown in FIG. 1 may be composed of yttria stabilized zirconia (YSZ). In yet another embodiment, the substrate 102 may be composed of zirconia.

The glass layers 106 and 110 are layers of thermally conducting but electrically insulating materials that are interposed between the heater 104 and temperature sensing layer 108, and between the temperature sensing layer 108 on one side and the at least one of the electrode 112 and adhesion layer 114 on the other side, respectively. Such glass layers 106 and 110, composed of such thermally conducting but electrically insulating materials, allow heat to be transported across the gas sensor 100, yet inhibit electrical contact between the heater 104 and the temperature sensing layer 108, and between the temperature sensing layer 108 on one side and the at least one of the electrodes 112 and adhesion layer 114 on the other side, respectively. Examples of suitable materials for the glass layers 106, 110 include, but are not limited to, polysilicate glass, silicon dioxide, silicon nitride, and any combinations thereof. The glass layer 110 may also be subjected to physical and chemical treatments to enable enhanced physical adhesion of the at least one electrode 112 and adhesion layer 114 to itself. Further, varying thicknesses of glass layers 106, 110 should allow for different amounts of heat links and electrical resistances between their respective enclosing layers.

In one embodiment, the dopant in the gas sensing layer 118 may be selected from the group consisting of Li, Na, K, Rb, Cs, Mg, Ca, Sr, Ba, V, Cu, Zr, Hf, Al, Si, P, Tb, Ti, Mn, Fe, Co, Ni, Zn, Y, Nb, Mo, Ru, Rh, Pd, La, Ta, W, Ga, In, Sb, Bi, Ce, Sm, Gd, Cd, Re, Pt, Ge, Cr, Pb, Lu, Nd, Pr, Eu, and combinations thereof. In another embodiment, the dopant in the gas sensing layer 118 can be selected from the group consisting of Re, Ni, V, Ta, Nb, Mo, Zr, and combinations thereof.

In one embodiment, the oxidation state of the one or more dopant species, when present in the host component of the gas sensing layer, may be such that the one or more dopant species are of n-type, p-type, or neutral type, or combinations thereof. Examples of such (host, dopant) pairs, wherein the dopant is of n-type may include, but are not limited to (tantalum oxide, Re and/or Cr), (tungsten oxide, Re and/or Mn). Examples of such (host, dopant) pairs, wherein the dopant is of p-type may include, but are not limited to (tantalum oxide, Zr and/or Hf), (tungsten oxide, Ta and/or Nb and/or V). Examples of such (host, dopant) pairs, wherein the dopant is of neutral type may include, but are not limited to (tantalum oxide, Nb), (tungsten oxide, Mo).

In one embodiment, the gas sensing layer may be composed of more than one material selected from the group represented by the chemical formula $L_\alpha M_\beta O_\gamma$, wherein L is a chemical element selected from the group consisting of Li, Na, K, Rb, Cs, Mg, Ca, Sr, Ba, V, Cu, Zr, Hf, Al, Si, P, Tb, and combinations thereof, and M is a chemical element selected from the group consisting of Ti, Mn, Fe, Co, Ni, Zn, Y, Nb, Mo, Ru, La, Ta, W, Ga, In, Sn, Sb, Bi, Ce, Sm, Gd, and combinations thereof, and $\alpha$, $\beta$, $\gamma$, are self-consistent. Examples of suitable materials from which the gas sensing layer may be composed include, but are not limited to, $Ta_2O_5$, $Tb_3Fe_5O_{12}$, $La_{0.8}Sr_{0.2}MnO_3$. In one embodiment, the gas sensing layer may be composed of more than one metal oxide compound, wherein the said metal is selected from the group consisting of W, Ta, and Nb. In the situation wherein the said gas sensing layer is composed of more than one material, the more than one material together may be present in forms, including but not limited to, mixture, solid solution, and combinations thereof. Suitable non-limiting examples of such mixtures include $CeO_2$—$Sm_2O_3$.

In one embodiment, when the gas sensing layer of the gas sensor is composed of a material represented by the chemical formula $L_\alpha M_\beta O_\gamma$, enhanced $NO_x$ response characteristics may be obtained for particular choice of L and M.

In one embodiment, when the gas sensing layer of the gas sensor is composed of a material represented by the chemical formula $L_\alpha M_\beta O_\gamma$, enhanced $NO_x$ response characteristics may be obtained for particular choice of L and M, and for particular amounts, $\alpha$ and $\beta$, of L and M respectively.

In one example, the response characteristics of the gas sensor to a given concentration of at least one analyte may be enhanced by varying the thickness and/or porosity of the gas sensing layer, when it is in the form of a thin film. In one embodiment, the thin film gas sensing layer 118 can have a thickness from about 10 nm to about 500 nm. In another embodiment, the thin film gas sensing layer 118 can have a thickness from about 50 nm to about 150 nm. In yet another embodiment, the thin film gas sensing layer 118 can have a thickness from about 70 nm to about 120 nm.

In one example, the response characteristics of the gas sensor 100 to a given concentration of at least one analyte may be enhanced by varying the thickness and/or porosity of the gas sensing layer 118, when it is in the form of a thick film. In one embodiment, the said thick film gas sensing layer 118 can have a thickness from about 500 nm to about 500 µm. In another embodiment, the said thick film gas sensing layer 118 can have a thickness from about 10 µm to about 300 µm. In yet another embodiment, the said thick film gas sensing layer 118 can have a thickness from about 20 µm to about 200 µm.

In one example, the response characteristics of the gas sensor 100 to a given concentration of at least one analyte may be enhanced by varying the thickness and/or porosity of the gas sensing layer 118, when it is in the form of a pellet. In one embodiment, the pellet gas sensing layer 118 can have a thickness from about 500 µm to about 3 mm. In another embodiment, the pellet gas sensing layer 118 can have a thickness from about 1 mm to about 3 mm. In yet another embodiment, the pellet gas sensing layer 118 can have a thickness from about 1 mm to about 2 mm.

In one embodiment, the response of the gas sensor, or of the material composing a sensing layer of the gas sensor, may be monitored via resistive measurement, potentiometric measurement, thermal measurement, or combinations thereof. The said thermal measurement, may be performed via several techniques, including but not limited to thermal imaging via infra-red camera.

A response modification layer 116 is interposed between the gas sensing layer 118 and the adhesion layer 114. In one embodiment, this response modification layer 116 may be composed of a material selected from the group consisting of Mg, V, Cu, Zr, Hf, Al, Si, Ti, Mn, Fe, Co, Ni, Zn, Nb, Mo, Ru, Rh, Pd, La, Ta, W, In, Sn, Sb, Bi, Sm, Re, Pt, Ge, Cr, and combinations thereof. In another embodiment, this response modification layer 116 may be composed of a material selected from the group consisting of Ti, Re, Ni, Ta, Nb, Mo, Zr, and combinations thereof. In one embodiment, the response modification layer 116 can have a thickness from about 10 Å to about 100 Å. In another embodiment, the response modification layer 116 can have a thickness from about 20 Å to about 80 Å. In yet another embodiment, the response modification layer 116 can have a thickness from about 30 Å to about 60 Å. In one embodiment of the gas sensor, the response modification layer may aid the gas sensor in having an equisensitive response to any two given gases. In another embodiment of the gas sensor 100, the response modification layer 116 may aid the gas sensor in having a desired value of baseline resistance. In yet another embodiment, the response modification layer may aid the gas sensor 100 in having a desired level of stability of baseline resistance with exposure over time to one or more analytes. In yet another embodiment of the gas sensor 100, the response modification layer 116 may aid the gas sensor in having desired levels of response and recovery times upon exposure to and withdrawal of analyte respectively. Not to be limited by any particular theory, it is possible that the response modification layer 116 helps improve the working characteristics of the gas sensor 100 by preventing direct physical contact between the gas sensing layer 118 and the adhesion layer 114.

In one embodiment, the response modification layer 116 may be composed of a mixture of Ti with at least one chemical element selected from the group consisting of Mg, V, Cu, Zr, Hf. Al, Si, Mn, Fe, Co, Ni, Zn, Nb, Mo, Ru, Rh, Pd, La, Ta, W, In, Sn, Sb, Bi, Sm, Re, Pt, Ge, Cr, and combinations thereof.

The adhesion layer 114 serves to anchor the response modification layer 116, upon which is disposed the gas sensing layer 118. The adhesion layer 114 may be composed of at least one chemical element selected from the group Ti, Cr, and combinations thereof. In one embodiment, the adhesion layer 114 can have a thickness from about 5 Å to about 100 Å. In another embodiment, the adhesion layer 114 can have a thickness from about 10 Å to about 50 Å. In yet another embodiment, the adhesion layer 114 can have a thickness from about 15 Å to about 30 Å.

The at least one of the electrodes 112 may be made from any material capable of physical adhesion and electrical contact to its adjacent layers. Examples of suitable materials for the at least one electrode 112 include, but are not limited to, Pt, Pd, Au, Ag, Ni, Ti, In, Sn, Cr, nickel oxide, nickel nitride, titanium nitride, aluminum doped zinc oxide, indium tin oxide, and any combination thereof.

In one embodiment, the at least one of the electrodes 112 can have a thickness from about 500 Å to about 10000 Å. In another embodiment, the at least one of the electrodes 112 can have a thickness from about 800 Å to about 3000 Å.

In one embodiment, the at least one of the electrode 112 may be a multilayer stack of materials. Examples of suitable materials to comprise the different layers of the multilayer stack include, but are not limited to, Pt, Pd, Ti, Al, Au, Ag, Ni, Cr, In, titanium nitride, nickel oxide, aluminum doped zinc oxide, nickel nitride, indium tin oxide, chrome, and any combination thereof.

In one embodiment in which the at least one of the electrodes 112 is a multilayer stack of materials, the thickness of each layer can be from about 100 Å to about 2000 Å. In another embodiment, in which the at least one of the electrodes is a multilayer stack of materials, the thickness of each layer can be from about 300 Å to about 1500 Å. In yet another embodiment, in which the at least one of the electrodes 112 is a multilayer stack of materials, the thickness of each layer can be from about 500 Å to about 1000 Å.

Figure 2:
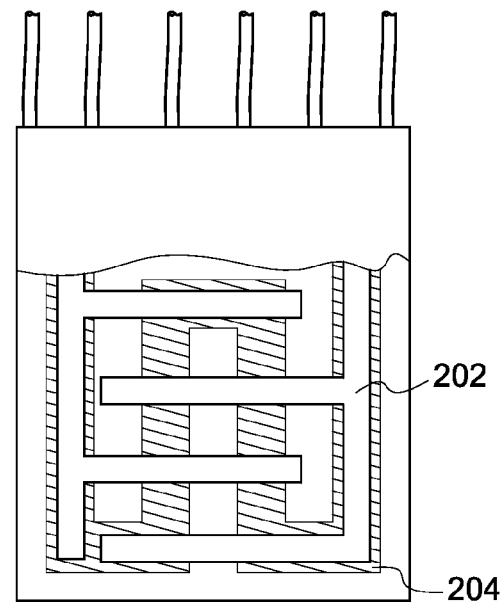
FIG. 2 is a diagrammatical representation of the top view of interdigitated electrodes in a $NO_x$ gas sensor, in accordance with an exemplary embodiment of the invention.
Figure 3:
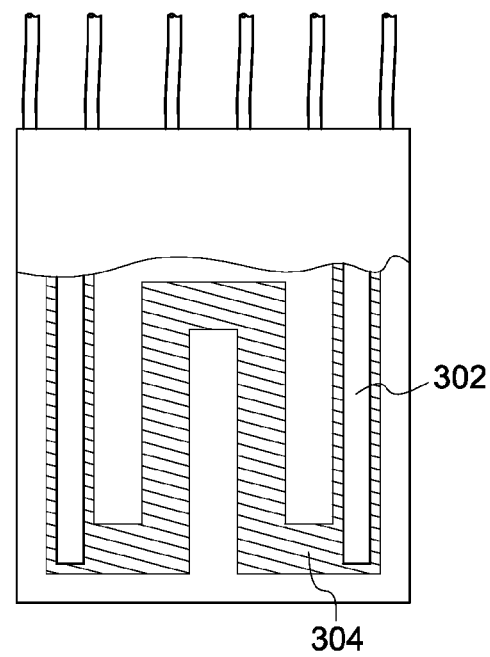
FIG. 3 is a diagrammatical representation of the top view of inline electrodes in a $NO_x$ gas sensor, in accordance with another exemplary embodiment of the invention.

In one embodiment, the at least one of the electrodes 112 can be placed in an interdigitated geometry 202 as shown in the gas sensor 200 in FIG. 2. Element 204 shows the geometry of underlying heater 104. In another embodiment, the at least one of the electrodes 112 can be placed in an inline geometry 302 as illustrated in the gas sensor 300 in FIG. 3. Element 304 shows the geometry of underlying heater 104.

In one embodiment, the at least one electrode 112 may be placed adjacent to the gas sensing layer 118 in a "sandwich" geometry, i.e., the at least one electrode 112 is disposed on either side of the gas sensing layer 118 along its thickness direction. In another embodiment, the at least one electrode 112 may be placed in a "side-by-side" geometry, i.e., at least two electrodes are disposed adjacent each other on the same side of the gas sensing layer 118. In another embodiment, a adhesion layer may be placed along those surfaces of the at least one electrode 112 that are closest to adjacent components of the gas sensor 100.

In one embodiment, the gas sensing layer 118 can have a dopant concentration from about 0 mol % to about 5 mol %. In another embodiment, the gas sensing layer 118 can have a dopant concentration from about 0.01 mol % to about 5 mol %. In yet another embodiment, the gas sensing layer 118 can have a dopant concentration from about 0.2 mol % to about 5 mol %. In yet another embodiment, the gas sensing layer 118 can have a dopant concentration from about 0.5 mol % to about 4 mol %. In yet another embodiment, the gas sensing layer 118 can have a dopant concentration from about 1 mol % to about 3 mol %.

In some embodiments, the gas sensor may include a way of measuring the temperature of the device. A means of measuring the temperature may be disposed anywhere within or close to the gas sensor. For example, it may be disposed adjacent to the gas sensing layer or, adjacent to the substrate layer, or on the packaging, or any combination thereof, and/or be covered with an electrically insulating and thermally conducting layer. Examples of temperature sensors include, but are not limited to, a resistive temperature device, a thermocouple, a silicon bandgap temperature sensor, a thermistor, infra-red camera, and combinations thereof. The temperature sensing means may be a separate element, such as a metal (e.g., Pt) layer disposed adjacent to the gas sensing layer.

The thermocouple temperature sensor can be of various types, including but not limited to Type K (CHROMEL®/ALUMEL®), Type J (Iron/Constantan), Type N(NICROSIL®), Type B, Type R, Type S, Type T (Copper/Constantan), Type C. The resistance temperature sensor can be composed of various metals, but are usually made from Pt. The silicon bandgap temperature sensor can be composed of pure silicon or of chemical compounds of silicon including, but not limited to, silicon carbide. The thermistor temperature sensor can be composed of various materials including but not limited to ceramics and polymers. These materials can have a positive or a negative temperature coefficient of resistance. The temperature sensors may be biased in various ways, including but not limited to, voltage biasing and current biasing. Furthermore, the response of the temperature sensors may be recorded by means including but not limited to resistive measurement, potentiometric measurement and a combination thereof.

Other gas sensor operating and geometry parameters being fixed, the response to a given concentration of any particular analyte may be optimal when the gas sensing layer is maintained at particular temperatures. In certain embodiments, optimal sensitivity may be achieved by maintaining the temperature within the range from about 300° C. to about 550° C.

Conceivably, different applied direct current (DC), alternating current (AC), or a combination thereof, of bias levels to the gas sensing layer may optimize the gas sensing characteristics such as selectivity and sensitivity towards one or another analyte. For example, according to some embodiments, varying levels of a DC bias may be used to adjust the sensitivity of the gas sensor 100 to different gas species in an analyte. For example, a gas sensor operating under a given first DC bias level might be preferentially sensitive to a first analyte species, a gas sensor operating under a second DC bias level might be preferentially sensitive to a second analyte species, and so on for different DC bias levels. This property may be used to selectively detect and measure different species of analyte. The AC and/or DC bias used in the operation of the gas sensor may be an electrical current, an electrical voltage or a combination thereof. The AC or DC response of the gas sensor during operation of the gas sensor may be an electrical current, an electrical voltage or a combination thereof.

The gas sensor also may be configured to have suitable filters that allow only specific analytes to pass through and impinge onto, i.e., make contact with, the gas sensing layer. Conceivably, such filter(s) may aid selective detection of given one or more analytes. Such filter(s) also may aid in limiting the passage of certain analytes such as, for instance, particulate matter, towards the gas sensing layer. In some embodiments, membranes that serve as filters towards particular chemical or physical species present in the environment of the gas sensor may be disposed adjacent to the gas sensing layer. Such filters would provide a means for limiting or regulating the type and/or the amount of gas or particulate species that contact the gas sensing layer of the gas sensor. Examples of suitable means for limiting or regulating the type and/or amount of gas species include, but are not limited to, a thin film porous membrane filter medium (e.g., steel wool or quartz wool), an about 10 Å thick film of Pd, porous ceramic materials such as $Al_2O_3$, YSZ, $SiO_2$, and any combinations thereof. Conceivably, more than one gas sensor may be placed adjacent to each other or at different locations within the environment. Each of these gas sensors may share with each other the same filter, or may individually have one or more, same or different filters. Such an "array" of gas sensors may be used to selectively detect and/or measure the concentrations of different analyte species at different locations within the environment. Conceivably, an "array" of more than one gas sensing layer, of same or different composition, may be placed adjacent to each other, so that the said more than one sensing layers share the same platform, or each one of the said more than one sensing layers possess their own platform, or combinations thereof.

In one embodiment, the porosity of a given gas sensing layer may be tuned to that it allows one or more specified analytes to pass through itself.

Figure 4:
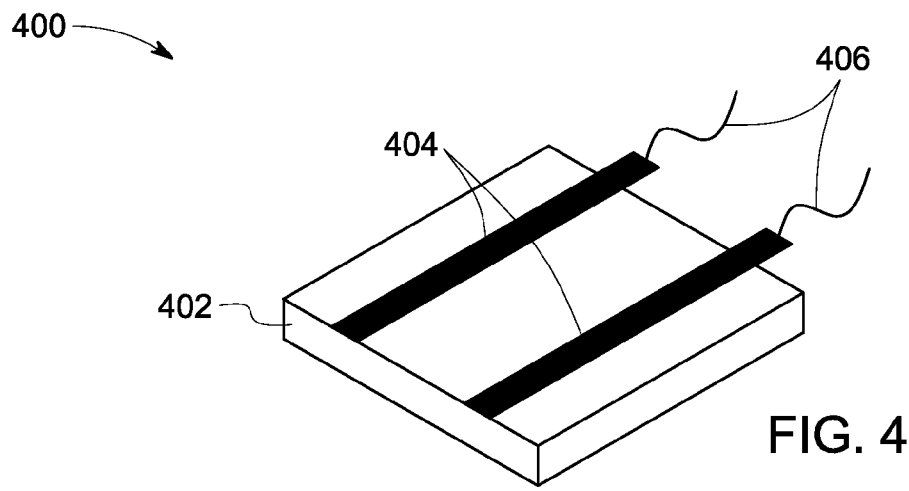
FIG. 4 is a diagrammatical representation of the placement of the electrodes on a sensing layer of the gas sensor wherein the electrodes are placed in a side-by-side geometry, in accordance with another exemplary embodiment of the invention.
Figure 5:
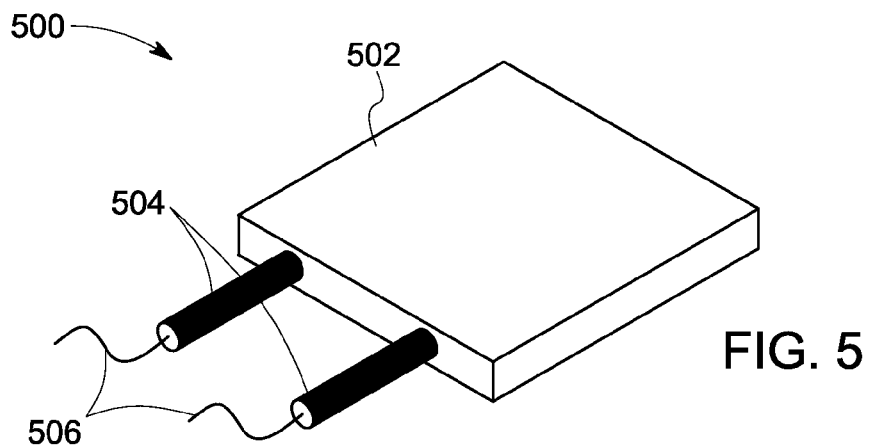
FIG. 5 is a diagrammatical representation of the placement of the electrodes on a sensing layer of the gas sensor wherein the electrodes are placed in a embedded geometry, in accordance with another exemplary embodiment of the invention.
Figure 6:
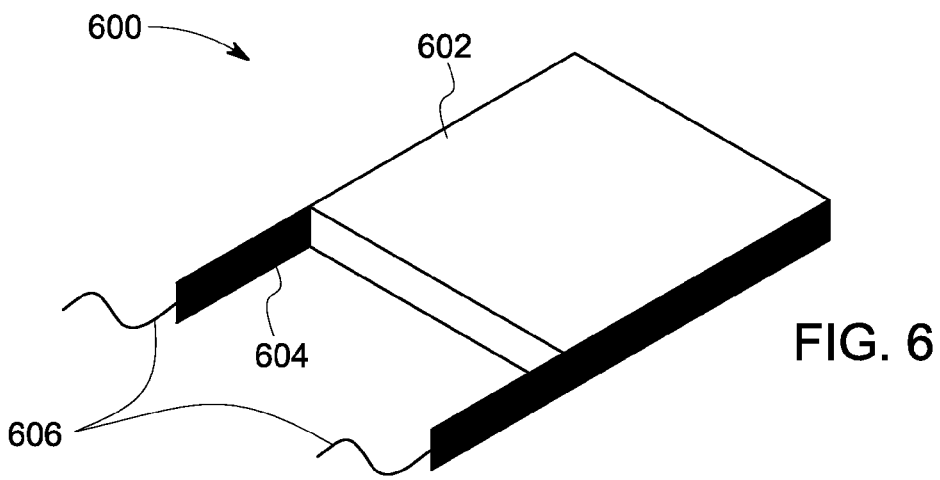
FIG. 6 is a diagrammatical representation of the placement of the electrodes on a sensing layer of the gas sensor wherein the electrodes are placed in a extremity geometry, in accordance with another exemplary embodiment of the invention.

In one embodiment 400 shown in FIG. 4, the at least one electrode 112 on the gas sensing layer 402 may be placed in a side-by-side geometry 404, and wires 406 of suitable electrically conducting material may be attached to said electrodes by suitable means. In one embodiment 500 shown in FIG. 5, the at least one electrode 112 on the gas sensing layer 502 may be placed in an embedded geometry 504, and wires 506 of suitable electrically conducting material may be attached to said electrodes by suitable means. In one embodiment 600 shown in FIG. 6, the at least one electrode 112 on the gas sensing layer 602 may be placed in an "extremity" geometry 604, and wires 606 of suitable electrically conducting material may be attached to said at least one electrode by suitable means. In one embodiment, suitable combinations of electrode geometries of 404, 504, and 604, may be used. The said at least one electrode can be shaped in any suitable shape, including but not limited to, rectangular, circular, point, and combinations thereof.

Figure 7:
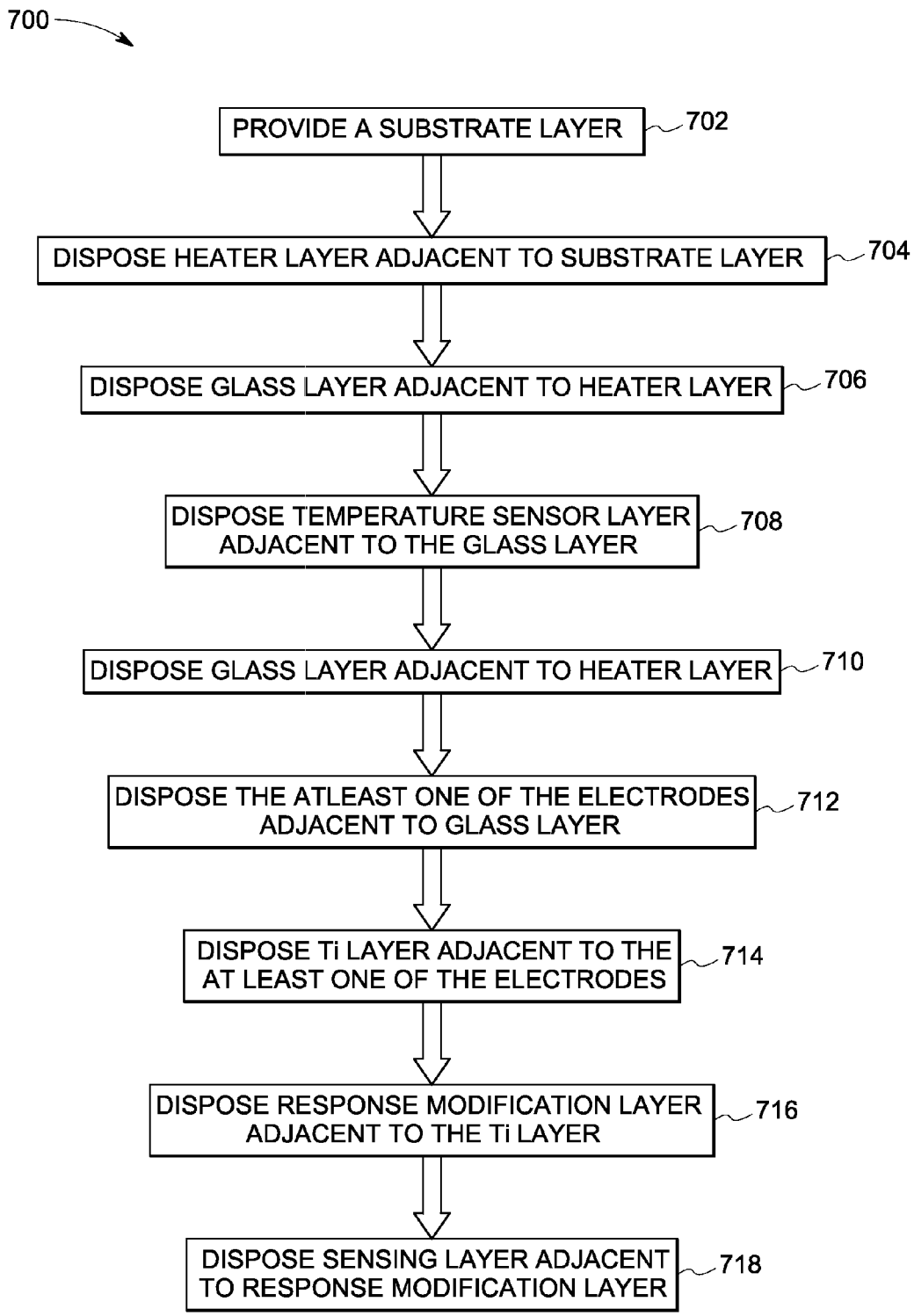
FIG. 7 is a flow chart representation of a manufacturing process of a $NO_x$ gas sensor in accordance with an exemplary embodiment of the invention.

FIG. 7 is a flow chart illustrating a method 700 for manufacturing the gas sensor in accordance with an exemplary embodiment of the invention. At step 702, a substrate layer, such as substrate layer 102 is provided. At step 704, a heater layer, such as heater layer 104, is disposed adjacent to the substrate layer. At step 706, such as first glass layer 106, a first glass layer is disposed adjacent to the heater layer, followed by step 708, where a temperature sensing layer, such as temperature sensing layer 108, is disposed adjacent to the glass layer. At step 710, a second glass layer, such as second glass layer 110, is disposed adjacent to the temperature sensing layer. At step 712, at least one electrode, such as at least one electrode 112, is disposed adjacent to the insulating layer. At step 714, a adhesion layer, such as adhesion layer 114, is disposed adjacent to the at least one electrode. At step 716 a response modification layer, such as response modification layer 116, is disposed adjacent to the adhesion layer. At step 718, a gas sensing layer, such as gas sensing layer 118, is disposed adjacent to the response modification layer.

Figure 8:
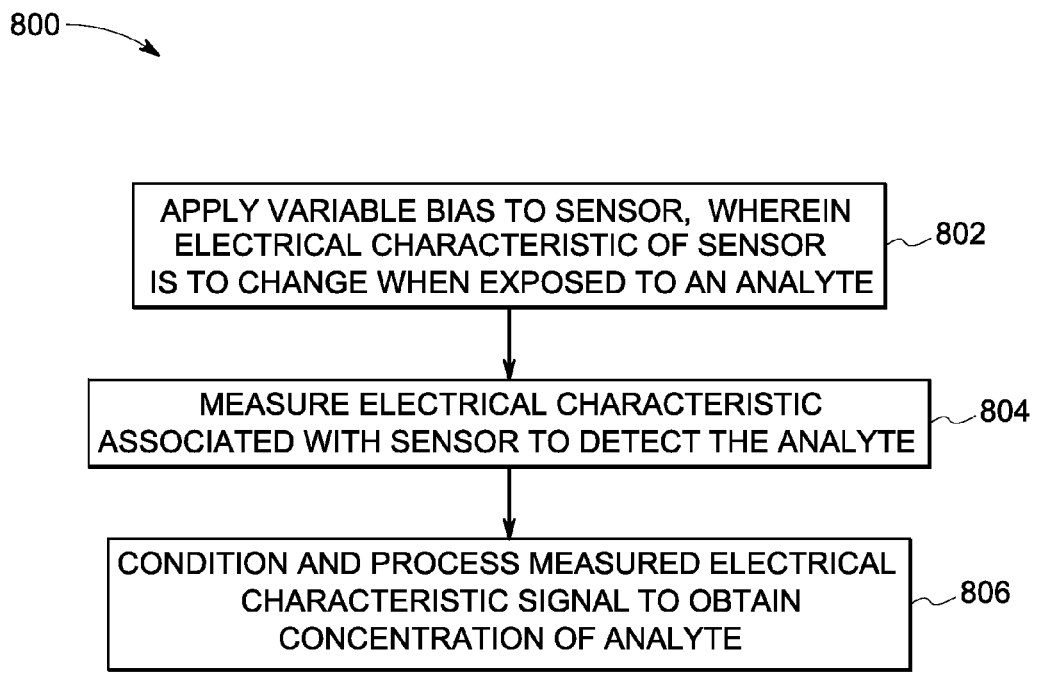
FIG. 8 is a flow chart representation of a method for detecting the analyte in accordance with one exemplary embodiment of the invention.

FIG. 8 is a flow chart illustrating a method 800 for detecting an analyte according to an embodiment of the invention. At step 802, an analyte is allowed to impinge upon the gas sensing layer of the gas sensor causing a change in an electrical characteristic of the gas sensor. In step 804, the change in the electrical characteristic, which is being monitored continuously, is detected. If the functional relationship between the change in the electrical characteristic and the concentration of the applied analyte is known, then one may determine the concentration of the applied analyte from the measured change in the electrical characteristic, as is shown in step 806. Examples of suitable electrical characteristics include, but a are not limited to, electrical resistance, electrical capacitance, electrical current, electrical voltage, and a combination thereof. As an example, if the gas sensor is used under voltage bias conditions, the electrical characteristic might be, for instance, electrical current. Furthermore, such response signals might be monitored continuously to determine information about time evolution of concentration of an analyte.

In one embodiment, the response of the gas sensor may be tuned to be equisensitive to NO and $NO_2$ which are the two primary constituents of $NO_x$ emissions. The response characteristics, including but not limited to, the response ratio of the gas sensor for different concentrations of $NO_x$ may depend upon a plurality of system parameters, including but not limited to, the level of oxygen deficiency in the gas sensing layer, the one or more dopants that are doped in host component of the gas sensing layer, the level of doping of the dopant, the microstructure/morphology of the gas sensing layer, the level of crystallinity of the gas sensing layer, the level of strain present in the gas sensing layer, the level of strain present in the adhesion layer, the level of strain present in the response modification layer, the temperature at which the gas sensing layer is maintained while performing the gas sensing, the type and nature of the bias applied across the gas sensing layer, the presence or absence of the response modification layer, the level of adhesion of the gas sensing layer to the electrodes and to the underlying glass, the porosity and/or packing fraction of the gas sensing layer, the porosity of the response modification layer, the material, size, design, and placement of the electrodes. The microstructure/morphology of the gas sensing layer film may depend on the method used to grow the film. Some of the above mentioned system parameters are likely inter-related. In another embodiment the response characteristics, including but not limited to, the response ratio of the gas sensor for different concentrations of $NO_x$ may depend upon a plurality of environment parameters, including but not limited to, the specific set of gas species that are present in the environment and on the individual concentrations of the different species present. For example, the relative humidity of the environment where the gas sensor is placed, may be a factor affecting the response characteristics of the gas sensor.

In one embodiment, the one or more dopants that are incorporated into the gas sensing layer may aid in modifying one or more response characteristics of the gas sensor, including but not limited to, baseline resistance, stability of baseline resistance over time, stability of baseline resistance with temperature, stability of baseline resistance over gas composition, response time, recovery time.

In the following measurements presented, the components of the sensor used may be grouped into two distinct sets depending on their source of origin and/or procurement. The five layers, i.e., the substrate 102, the heater 104 the first glass layer 106, the temperature sensing layer 108, and the second glass layer 110 were sourced from a commercial vendor. All other elements, i.e., the electrodes 112, the adhesion layer 114, the response modification layer 116, and the gas sensing layer 118, were designed and implemented by the inventors.

In one embodiment, the material composing the gas sensing layer of the gas sensor was prepared in a mixture powder form according to the following protocol: About 3 grams of tungsten oxide ($WO_{2.9}$ or $WO_3$) powder and a required amount of powder or solution of a suitable salt of a desired one or more dopant were taken and ground well with IPA (iso-propyl alcohol) or water in an agate pestle and mortar. Suitable salts of the one or more dopants may include, but are not limited to, oxides, nitrates, sulphates, and carbonates. The resulting mixture was dried at room temperature or at a temperature of about 100° C. in a oven, and a powder was obtained. This powder was heat treated in a furnace in a air/(1% $H_2+N_2$) atmosphere. The temperature of heat treatment was between 500° C. to 1000° C. depending on the particular dopant or dopants be incorporated into the host component of the gas sensing layer. The powder was then allowed to cool to room temperature to obtain a mixture powder of the doped tungsten oxide. In another embodiment, the material composing the gas sensing layer of the gas sensor was prepared in a blend form according to the following protocol: About 3 grams of tungsten oxide ($WO_{2.9}$ or $WO_3$) powder and the required amount of powder or solution of a suitable salt of the desired one or more dopant were taken and ground well with IPA or water in an agate pestle and mortar. Suitable salts may include, but are not limited to, oxides, nitrates, sulphates, and carbonates. The resulting mixture was dried at room temperature or at a temperature of about 100° C. in a lab oven, and a blend powder of doped tungsten oxide was obtained. This blend powder was then allowed to cool to room temperature.

In one embodiment, a slurry of a material composing a gas sensing layer of the gas sensor was obtained as follows: about 0.126 gram of commercially available binder VOO6 (obtained from Heraeus™), and about 0.150 gram of terpineol were mixed in a mortar and pestle, as a previously obtained mixture powder or blend powder of doped tungsten oxide was introduced slowly. The addition of the mixture powder or blend powder was stopped when a consistency of the slurry was optimal for screen-printing. Not to be limited by any particular theory, the amount of doped tungsten oxide that need be introduced to obtain a slurry of optimal consistency, varies with size distribution of the particles from which is composed the mixture powder or blend powder of the doped tungsten oxide. Typically, the amount of doped tungsten oxide required to obtain a slurry of optimal consistency is from about 1.5 gram to about 2.2 gram.

In one embodiment, a gas sensing layer of the gas sensor was deposited via the method of screen-printing as follows: a substrate (on which are present Pt electrodes) was placed under a screen with optimal mesh spacing and optimal mesh pore size. An optimal amount of a previously obtained slurry was placed on top of the substrate above the screen mesh. This slurry was forced to pass through the mesh by giving 3-5 compressive movements using an evenly edged plastic screen-printing knife so that a film of the slurry was deposited on to the substrate. The screen and the substrate were now carefully separated and the slurry deposited on the substrate was allowed to dry overnight at room temperature. The thus obtained deposited film was subjected to heat treatment according to the following protocol: the said film was heated to about 300° C. at the rate of about 1° C. per minute in air atmosphere. Next the atmosphere was changed to air or ($H_2+N_2$), and the heating was continued at the rate of about 1° C. per minute up to a maximum processing temperature that is typically within the range from about 700° C. to about 1000° C. The temperature variation was discontinued after the maximum processing temperature is achieved so that the temperature was held constant for duration from about 1 hour to about 6 hours. Subsequently, the temperature was reduced to room temperature at the rate of about 5° C. per minute.

The method of manufacturing of the gas sensor in an embodiment wherein the gas sensing layer is deposited via the method of screen-printing, may be amenable for ready scaling up of production of gas sensors. Conceivably, the screen printing method of deposition of the gas sensing layer of the gas sensor may allow for ready control of morphology of the gas sensing layer, including but not limited to factors such as porosity and packing fraction.

In another embodiment, a gas sensing layer was obtained in a pellet form as follows: a previously obtained mixture powder or blend powder was mixed with about 2 wt % PVA (poly-vinyl alcohol) binder solution. The thus obtained mixture was allowed to dry for an optimal amount of time to obtain a binder mixture. A required amount of the said binder mixture was now transferred to a suitable die, and pressed at a pressure between about 4 tons to about 8 tons using a manual or hydraulic press. The thus obtained pellet was removed from the die. The obtained pellet was subjected to heat treatment according to the following protocol: the pellet was heated to about 300° C. at the rate of about 1° C. per minute in air atmosphere. Next the atmosphere was changed to air or ($H_2+N_2$), and the heating was continued at the rate of about 1° C. per minute up to a maximum processing temperature that is typically within the range from about 700° C. to about 1000° C. The temperature variation was discontinued after the maximum processing temperature is achieved so that the temperature was held constant for duration from about 1 hour to about 6 hours. Subsequently, the temperature was reduced to room temperature at the rate of about 5° C. per minute. It is possible that a volume of the pellet undergoes a change during the said heat treatment.

In one embodiment, the porosity, and size and shape of the particles composing the powders that are used in the manufacture of the gas sensing layer of the gas sensor may influence the response characteristics of the gas sensor, including but not limited to, selectivity towards one or more analytes, sensitivity towards one or more analytes, response time upon exposure to one or more analytes, recovery time upon withdrawal of one or more analytes, baseline resistance, stability of baseline resistance, response ratio.

In some embodiments of the gas sensor, the host component of the gas sensing layer was composed of tungsten oxide. Typically, the powders that were used to form the said gas sensing layer had the composition $WO_{2.9}$ or $WO_3$. Typically, the powders of composition $WO_{2.9}$ were sourced from a commercial vendor and had a particle size (diameter) distribution that was unimodal, with mean value of about 34.8 µm and standard deviation of about 17.4 µm. On the other hand, the powders of composition $WO_3$ were sourced either from a commercial vendor, or were prepared in-house. The commercially sourced powders of composition $WO_3$ had a particle size distribution that was bimodal, with the two peaks being placed at about 5 µm and at about 12 µm. The homemade powders of composition $WO_3$ were obtained by pyrolysis of $H_2WO_4$ at about 500° C., and had a particle size distribution that was unimodal, with mean value of about 1.2 µm and standard deviation of about 0.6 µm.

Not to be limited by any particular theory, it is believed that response characteristics of the gas sensor, including but not limited to, response time, recovery time, and the sensitivity of the gas sensor to any given one or more analytes may be a function of the packing fraction of the gas sensing layer.

In one embodiment, the gas sensing layer as deposited may be subjected to annealing in the presence of hydrogen gas. Not to be limited to any particular theory, the said annealing in the presence of hydrogen may result in a loss of adhesion of the gas sensing layer on the adjacent layers in contact with itself.

In one embodiment, a certain amount of diffusion is expected to take place within the different layers constituting the gas sensor, i.e., adjacent layers may diffuse into each other where they meet.

The following results of measurements of the response of certain embodiments of the gas sensor were performed according to the following protocol: a mixture gas comprised of gases $O_2$ and $N_2$, in an ratio of 1:9 is made to flow within the chamber where the gas sensor is mounted. The flow rate of mixture gas is typically 1 slm (standard liters per minute). Specified amount between about 5 ppm to about 500 ppm of $NO_x$ gas are then introduced into the said flow for durations typically between 5 minutes to about 10 minutes. The response of the gas sensor, which is maintained at a temperature of about 400° C., is continuously monitored. Typically, the above measurements of response of the gas sensor are performed for a duration of about 72 hours. The response time is obtained from the time evolution of the response upon the introduction of the NO gas in to the sample chamber. The recovery time is determined in similar vein by switching off of the flow of the NO gas, all other conditions remaining identical. The flow of NO is withdrawn, typically for duration 20 or 30 minutes. The recovery time is obtained from the time evolution of the response upon the withdrawal of the NO gas in to the sample chamber. This sequence of steps may be repeated to determine the reproducibility of the response.

In one embodiment, the gas sensing layer of the gas sensor may need to be conditioned before it displays a desired and/or adequate response to any given one (or more) analyte(s). For example, when the method of deposition of the gas sensing layer is sputtering, then the as-deposited gas sensing layer is likely amorphous. This as-deposited gas sensing layer may not display desired or adequate response characteristics to, say, $NO_x$. Not to be limited by any particular theory, it is believed that changing the morphology of the gas sensing layer to tune its level of crystallinity, and/or grain size, and/or grain boundary interconnectivity, and/or porosity, and/or packing fraction and/or packing density, amongst other factors, will result in improved response characteristics of the gas sensor. It was determined that annealing the gas sensing layer at high temperatures in the presence of gases which contain nitrogen and oxygen (e.g., $NO_x$) resulted in the development, in the gas sensing layer, of desired response characteristics towards $NO_x$.

The following results of measurement of response characteristics of gas sensors were obtained on gas sensing layers that were about 150 μm along a thickness direction and in which the typical distance between the electrodes was 1 mm. Further, the cross-section area of the gas sensing layer, along the direction in which the resistance of the gas sensor was measured, were likely approximately equal.

Figure 9:
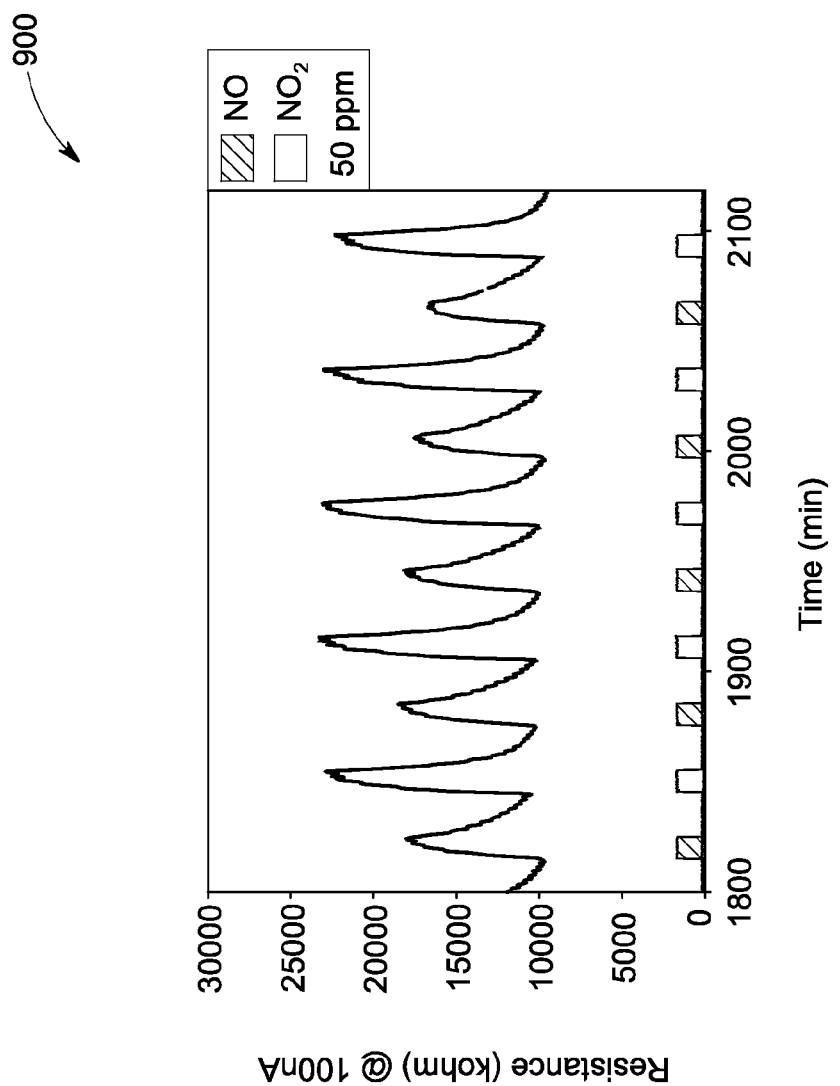
FIG. 9 is a graphical representation of the variation in gas sensor response upon exposure to 50 ppm NO gas level and 50 ppm $NO_2$ gas level, wherein the dopant species in a gas sensing layer of the gas sensor is Re, in accordance with one exemplary embodiment of the invention.

FIG. 9 is a graph 900 illustrating the resistance response of the gas sensor over time according to an exemplary embodiment of the invention when host component of the gas sensing layer is tungsten oxide that was obtained from powder of composition $WO_{2.9}$, and the dopant species in the host is Re. The measurements were performed in 4-terminal mode while passing a fixed current equal to 100 nA (nano Ampere) between the electrodes. Indicated levels of NO (50 ppm) and $NO_2$ (50 ppm) gas were applied successively to the gas sensor. The gas sensor was maintained at a temperature of about 400° C. when the measurements were performed. In this case, the response due to the presence of the first species and second species of analyte ($NO_2$ and NO respectively) induces a response (change in resistance) ratio, rr, that is, on the average, very nearly 1.5. The baseline resistance is stable over time with an estimated value of about 10000 kΩ.

Figure 10:
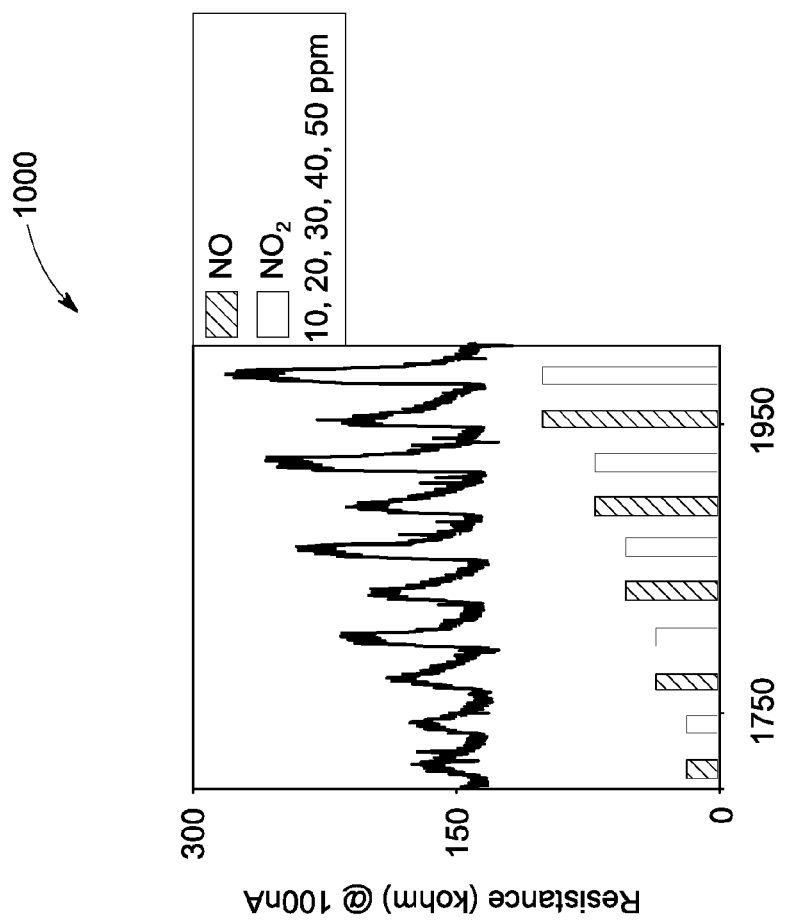
FIG. 10 is a graphical representation of the variation in gas sensor response upon exposure to different indicated NO and $NO_2$ gas levels, wherein the dopant species in a gas sensing layer of the gas sensor is V, in accordance with one exemplary embodiment of the invention.

FIG. 10 is a graph 1000 illustrating the resistance response of the gas sensor over time according to an exemplary embodiment of the invention when host component of the gas sensing layer is tungsten oxide that was obtained from powder of composition $WO_{2.9}$, and the dopant species in the host is V. The measurements were performed in 4-terminal mode while passing a fixed current equal to 100 nA (nano Ampere) between the electrodes. Different indicated ppm levels of NO and $NO_2$ gas were applied successively to the gas sensor. The gas sensor was maintained at temperature of about 450° C. when the measurements were performed. In this case, the response due to the presence of the first species and second species of analyte ($NO_2$ and NO respectively) induces a response (change in resistance) ratio, rr, that is, on the average, very nearly 1.5. The baseline resistance is stable over time with a estimated value of about 95 kΩ.

Figure 11:
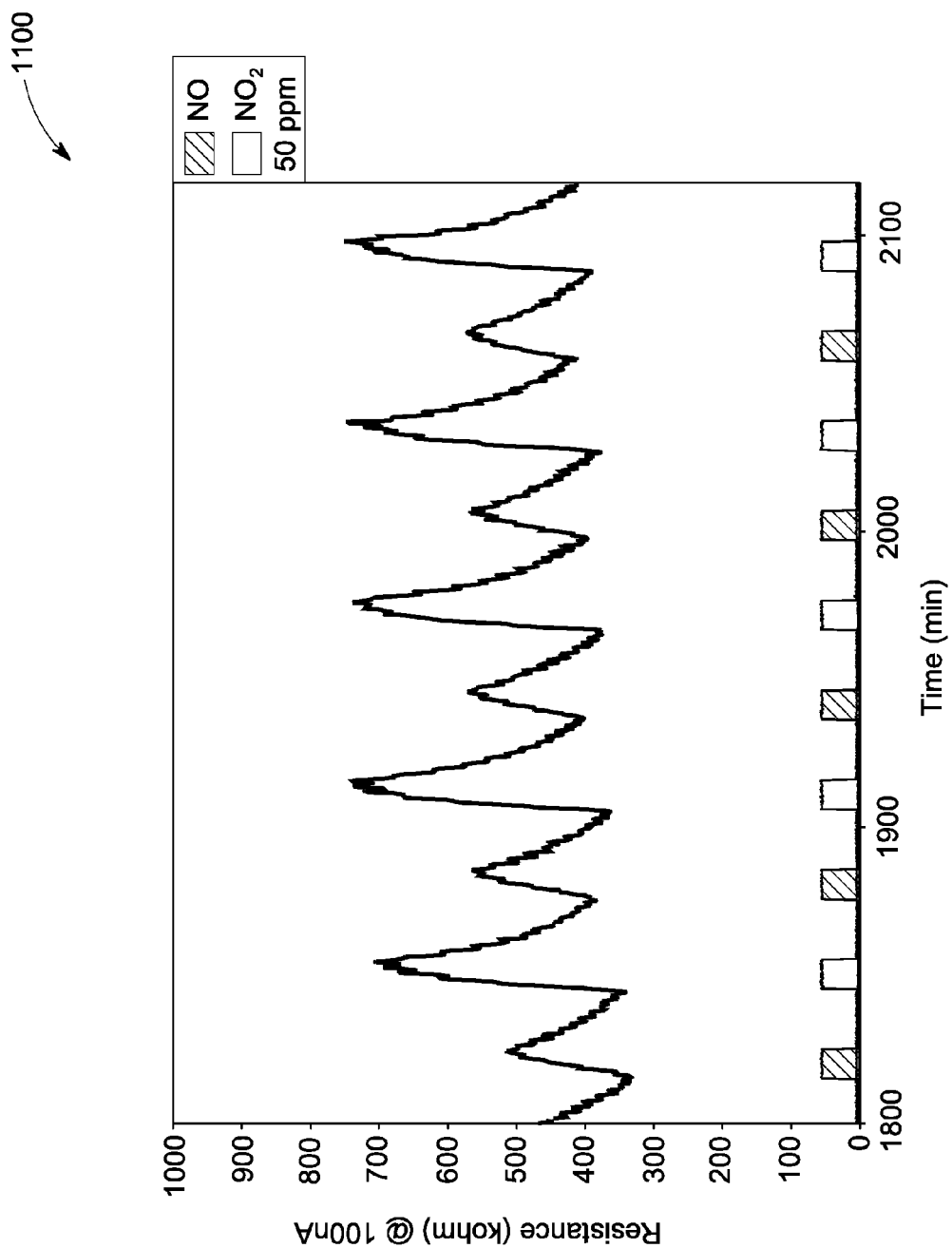
FIG. 11 is a graphical representation of the variation in gas sensor response upon exposure to 50 ppm NO gas level and 50 ppm $NO_2$ gas level, wherein two dopant species Re and V are incorporated in a gas sensing layer of the gas sensor, in accordance with one exemplary embodiment of the invention.

FIG. 11 is a graph 1100 illustrating the resistance response of the gas sensor over time according to an exemplary embodiment of the invention when host component of the gas sensing layer is tungsten oxide that was obtained from powder of composition $WO_{2.9}$, and there are present two dopant species in the host, namely, Re and V. The measurements were performed in 4-terminal mode while passing a fixed current equal to 100 nA (nano Ampere) between the electrodes. Indicated levels of NO (50 ppm) and $NO_2$ (50 ppm) gas were applied successively to the gas sensor. The gas sensor was maintained at temperature of about 400° C. when the measurements were performed. In this case, the response due to the presence of the first species and second species of analyte ($NO_2$ and NO respectively) induces a response (change in resistance) ratio, rr, that is, on the average, very nearly 2. The baseline resistance is stable over time with a estimated value of about 400 kΩ.

Not to be limited by any particular theory, it may be possible to tune the baseline resistance of the gas sensor by incorporating suitably chosen additional dopant species within the host component of the gas sensing layer of the gas sensor. For instance, comparing the baseline resistances of the gas sensors whose responses are shown in FIG. 9 and FIG. 11, one sees that when there are present 2 dopants (FIG. 11) namely, Re and V, the baseline resistance is lesser (having a estimated value of about 400 kΩ) than when there is present a single dopant (FIG. 9), namely Re (having a estimated value of about 10000 kΩ). In similar vein, not to be limited to any particular theory, it may be possible to tune the relative stability of the baseline resistance of the gas sensor by incorporating suitably chosen additional dopant species within the host component of the gas sensing layer of the gas sensor.

Figure 12:
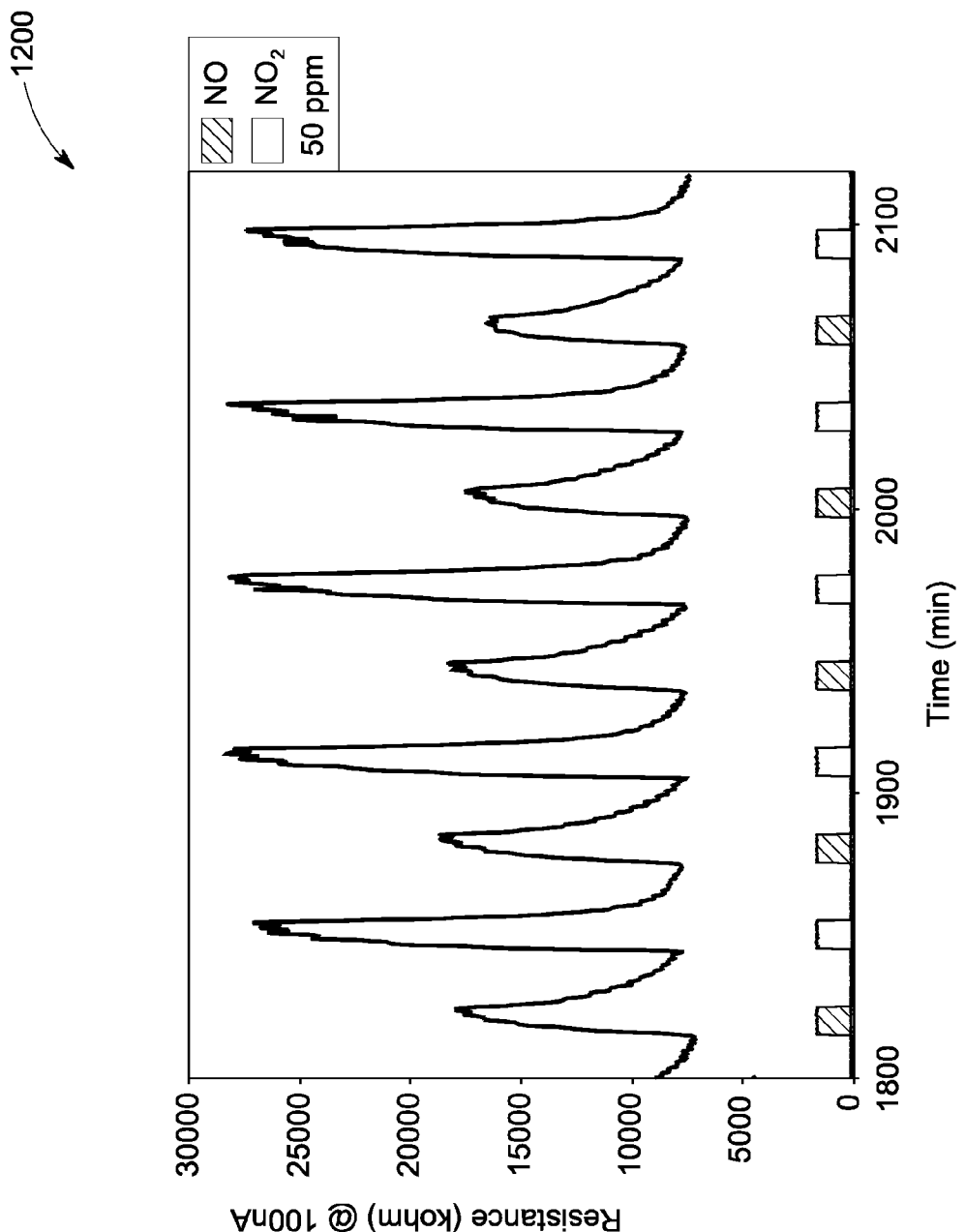
FIG. 12 is a graphical representation of the variation in gas sensor response upon exposure to 50 ppm NO gas level and 50 ppm $NO_2$ gas level, wherein two dopant species Zr and Re are incorporated in a gas sensing layer of the gas sensor, in accordance with one exemplary embodiment of the invention.

FIG. 12 is a graph 1200 illustrating the resistance response of the gas sensor over time according to an exemplary embodiment of the invention when host component of the gas sensing layer is tungsten oxide that was obtained from powder of composition $WO_{2.9}$, and there are present two dopant species in the host, namely, Zr and Re. The measurements were performed in 4-terminal mode while passing a fixed current equal to 100 nA (nano Ampere) between the electrodes. Indicated levels of NO (50 ppm) and $NO_2$ (50 ppm) gas were applied successively to the gas sensor. The gas sensor was maintained at temperature of about 400° C. when the measurements were performed. In this case, the response due to the presence of the first species and second species of analyte ($NO_2$ and NO respectively) induces a response (change in resistance) ratio, rr, that is, on the average, very nearly 1.5. The baseline resistance is stable over time with a estimated value of about 5000 k$\Omega$.

Figure 13:
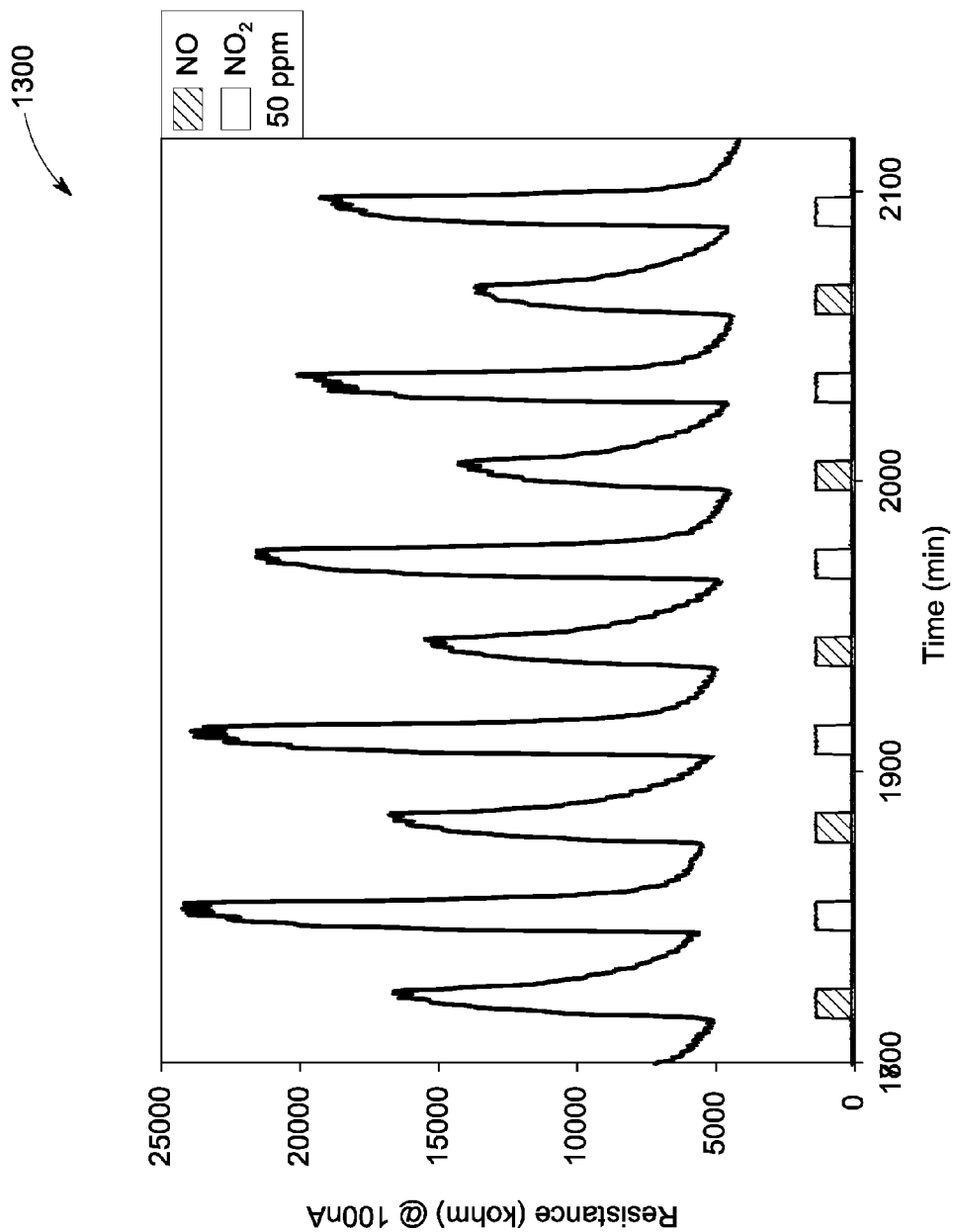
FIG. 13 is a graphical representation of the variation in gas sensor response upon exposure to 50 ppm NO gas level and 50 ppm $NO_2$ gas level, wherein two dopant species Ta and Re are incorporated in a gas sensing layer of the gas sensor, in accordance with one exemplary embodiment of the invention.

FIG. 13 is a graph 1300 illustrating the resistance response of the gas sensor over time according to an exemplary embodiment of the invention when host component of the gas sensing layer is tungsten oxide that was obtained from powder of composition $WO_{2.9}$, and there are present two dopant species in the host, namely, Ta and Re. The measurements were performed in 4-terminal mode while passing a fixed current equal to 100 nA (nano Ampere) between the electrodes. Indicated levels of NO (50 ppm) and $NO_2$ (50 ppm) gas were applied successively to the gas sensor. The gas sensor was maintained at temperature of about 400° C. when the measurements were performed. In this case, the response due to the presence of the first species and second species of analyte ($NO_2$ and NO respectively) induces a response (change in resistance) ratio, rr, that is, on the average, very nearly 2. The baseline resistance is stable over time with a estimated value of about 7500 k$\Omega$.

Not to be limited by any particular theory, it may be possible to tune the response time and recovery time of the gas sensor by incorporating suitably chosen one or more dopant species within the host component of the gas sensing layer of the gas sensor. For instance, comparing the recovery time of the gas sensor whose response is shown in FIG. 9, wherein a single dopant species Re is incorporated into the host component of the gas sensing layer, to the recovery time of the gas sensor whose response is shown in FIG. 12, wherein two dopant species, namely, Zr and Re, are incorporated into the host component of the gas sensing layer, one sees that the recovery time is faster for the gas sensor whose response is depicted in FIG. 12. In similar vein, comparing the recovery time of the gas sensor whose response is shown in FIG. 9, wherein a single dopant species Re is incorporated into the host component of the gas sensing layer, to the recovery time of the gas sensor whose response is shown in FIG. 13, wherein two dopant species, namely, Ta and Re, are incorporated into the host component of the gas sensing layer, one sees that the recovery time is faster for the gas sensor whose response is depicted in FIG. 13.

Figure 14:
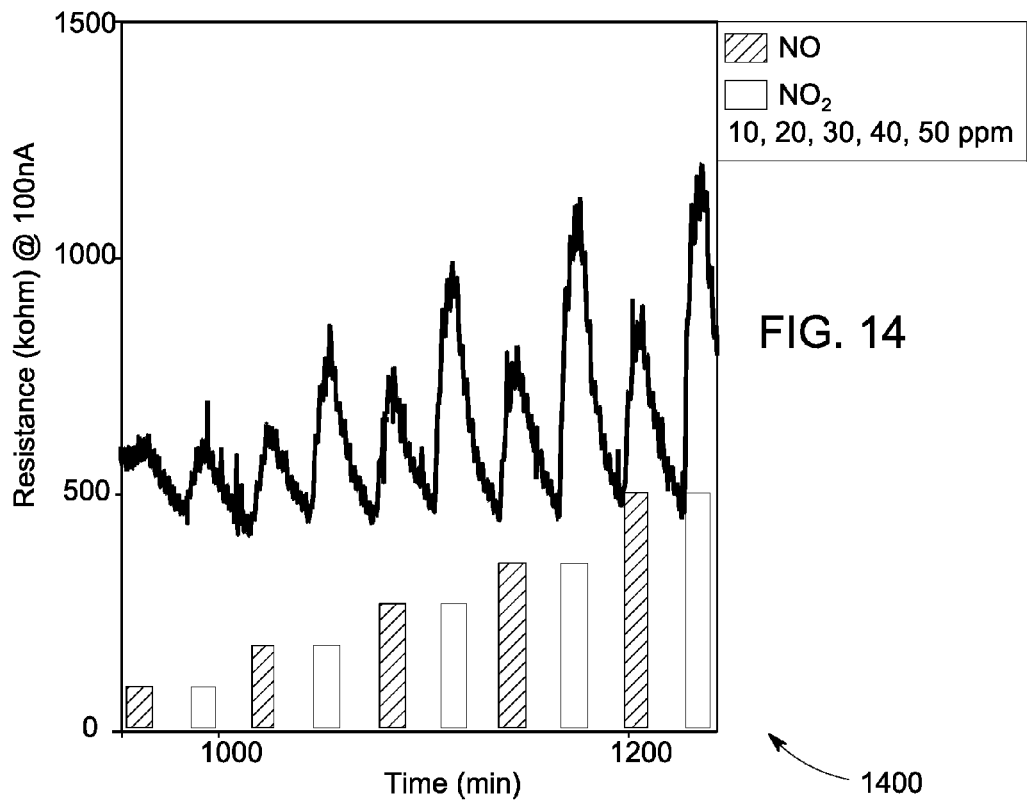
FIG. 14 is a graphical representation of the variation in gas sensor response upon exposure to different indicated NO and $NO_2$ gas levels, wherein the dopant species in a gas sensing layer of the gas sensor is V, in accordance with one exemplary embodiment of the invention.

FIG. 14 is a graph 1400 illustrating the resistance response of the gas sensor over time according to an exemplary embodiment of the invention when host component of the gas sensing layer is tungsten oxide that was obtained from powder of composition $WO_{2.9}$, and the dopant species in the host is V. The measurements were performed in 4-terminal mode while passing a fixed current equal to 100 nA (nano Ampere) between the electrodes. Different indicated ppm levels of NO and $NO_2$ gas were applied successively to the gas sensor. The gas sensor was maintained at temperature of about 400° C. when the measurements were performed. In this case, the response due to the presence of the first species and second species of analyte ($NO_2$ and NO respectively) induces a response (change in resistance) ratio, rr, that is, on the average, very nearly 1.5. The baseline resistance is stable over time with a estimated value of about 400 k$\Omega$.

Figure 15:
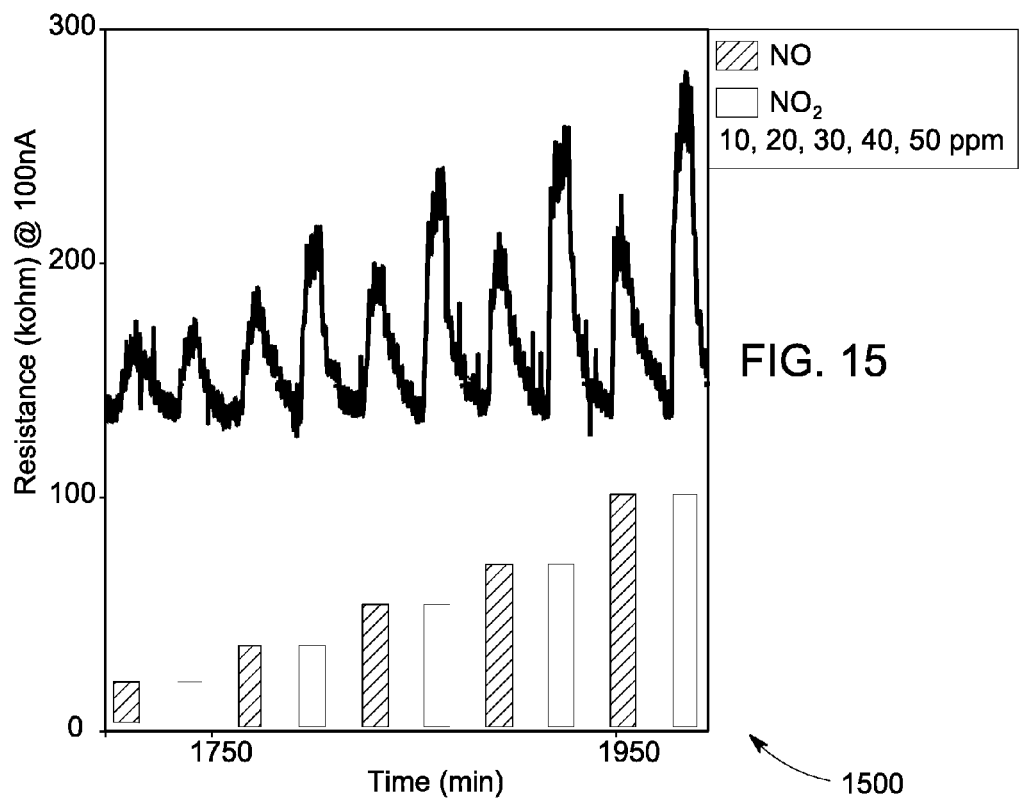
FIG. 15 is a graphical representation of the variation in gas sensor response upon exposure to different indicated NO and $NO_2$ gas levels, wherein the dopant species in a gas sensing layer of the sensor is V, in accordance with one exemplary embodiment of the invention.

FIG. 15 is a graph 1500 illustrating the resistance response of the gas sensor over time according to an exemplary embodiment of the invention when host component of the gas sensing layer is tungsten oxide that was obtained from powder of composition $WO_{2.9}$, and the dopant species in the host is V. The measurements were performed in 4-terminal mode while passing a fixed current equal to 100 nA (nano Ampere) between the electrodes. Different indicated ppm levels of NO and $NO_2$ gas were applied successively to the gas sensor. The gas sensor was maintained at temperature of about 450° C. when the measurements were performed. In this case, the response due to the presence of the first species and second species of analyte ($NO_2$ and NO respectively) induces a response (change in resistance) ratio, rr, that is, on the average, very nearly 1.5. The baseline resistance is stable over time with a estimated value of about 95 k$\Omega$.

Figure 16:
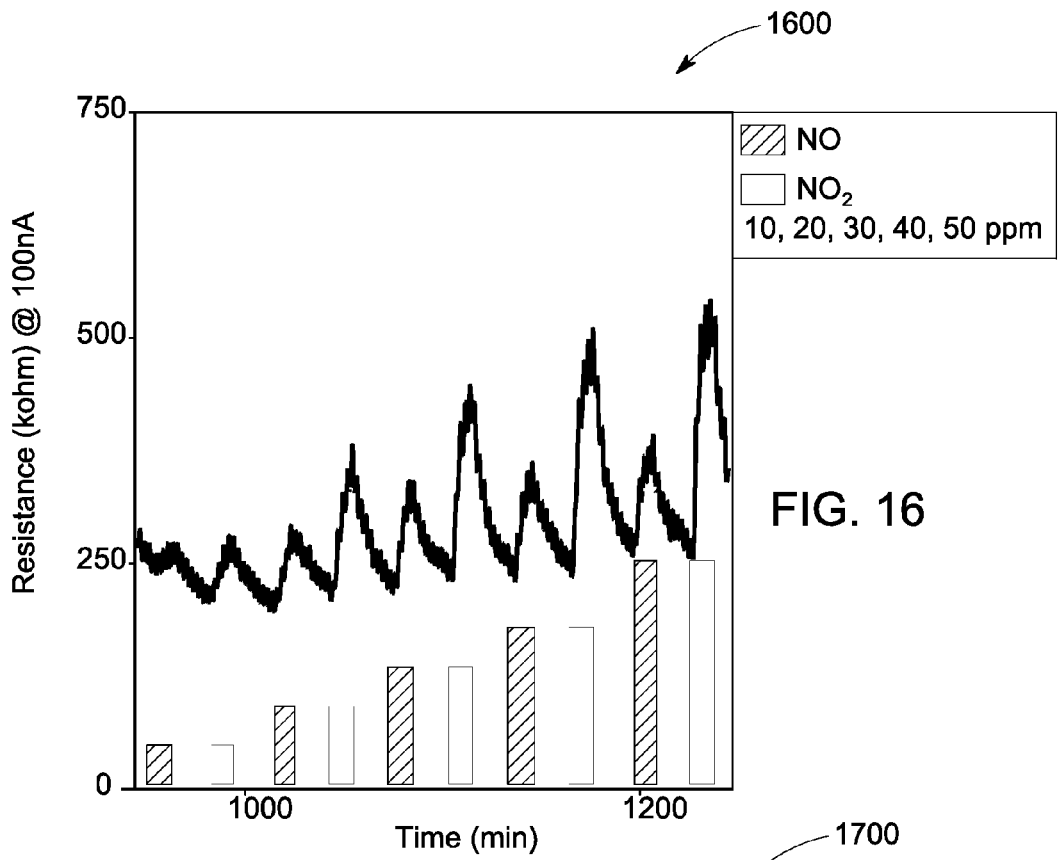
FIG. 16 is a graphical representation of the variation in gas sensor response upon exposure to different indicated NO and $NO_2$ gas levels, wherein two dopant species V and Re are incorporated in a gas sensing layer of the gas sensor, in accordance with one exemplary embodiment of the invention.
Figure 17:
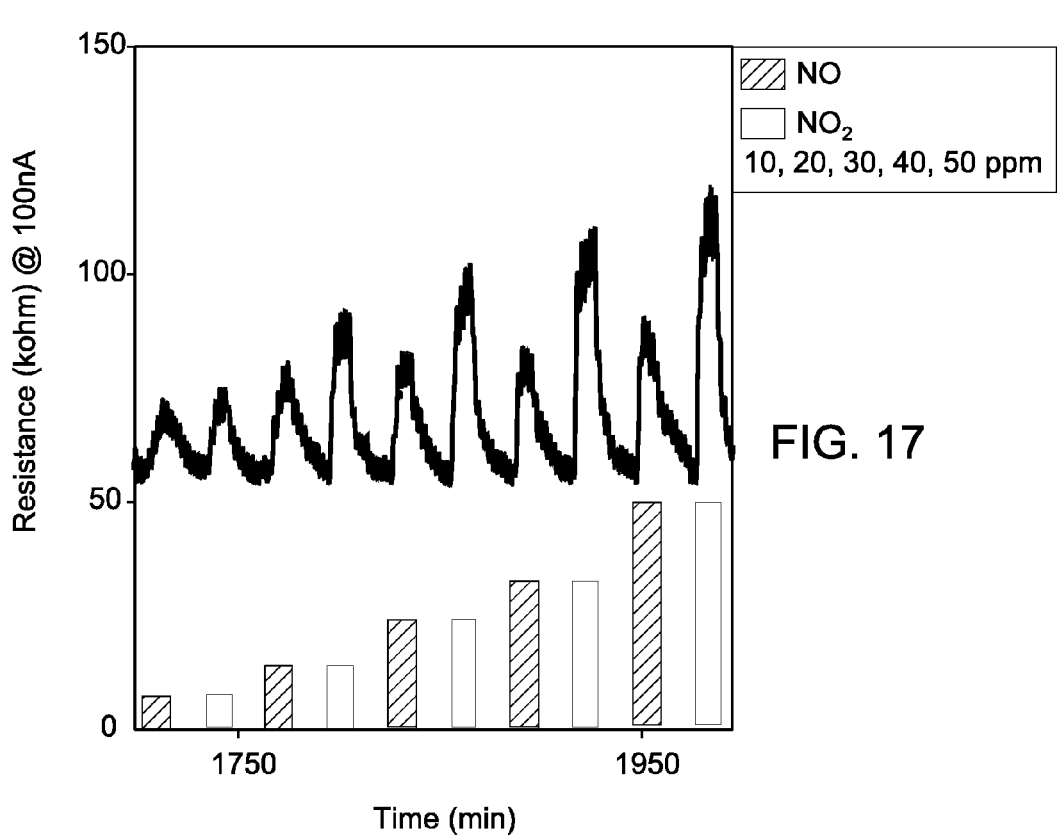
FIG. 17 is a graphical representation of the variation in gas sensor response upon exposure to different indicated NO and $NO_2$ gas levels, wherein two dopant species V and Re are incorporated in a gas sensing layer of the gas sensor, in accordance with one exemplary embodiment of the invention.

Not to be limited by any particular theory, for a given choice of one or more dopants incorporated into the host component of the gas sensing layer, it may be possible to tune the response characteristics of the gas sensor via the temperature at which the gas sensor is being maintained. For instance, comparing the baseline resistances of the gas sensor, wherein a single dopant V has been incorporated into the host component of the gas sensing layer, whose responses are shown in FIG. 14 and FIG. 15, one sees that when the temperature of the gas sensor is maintained at 450° C. (FIG. 15), the estimated value of the baseline resistance is 95 k$\Omega$, as opposed to when the temperature of the gas sensor is maintained at 400° C. (FIG. 14), wherein the estimated baseline resistance of the gas sensor is 400 k$\Omega$. In similar vein, it may be possible to tune the response and recovery times of the gas sensor via the temperature at which the gas sensor is maintained. Comparing once again the response and recovery times of the data shown in FIG. 14 and FIG. 15, one sees that the response time, as well as the recovery time, is faster when the gas sensor is maintained at temperature of about 450° C. (FIG. 15) as compared to when the gas sensor is maintained at a temperature of about 400° C. (FIG. 14). In similar vein, it may be possible to tune the stability of the baseline resistance of the gas sensor via the temperature at which the gas sensor is maintained. Comparing once again the stability of the baseline resistance of the data shown in FIG. 14 and FIG. 15, one sees that the stability of the baseline resistance improves when the gas sensor is maintained at temperature of about 450° C. (FIG. 15) as compared to when the gas sensor is maintained at a temperature of about 400° C. (FIG. 14). In similar vein, comparing the baseline resistances of the gas sensor, wherein two dopants, namely, V and Re, have been incorporated into the host component of the gas sensing layer, whose responses are shown in FIG. 16 and FIG. 17, one sees that when the temperature of the gas sensor is maintained at about 450° C. (FIG. 17), the estimated value of the baseline resistance is 40 k$\Omega$, as opposed to when the temperature of the gas sensor is maintained at about 400° C. (FIG. 16), wherein the estimated baseline resistance of the gas sensor is 150 k$\Omega$.

It has been estimated that the delay time associated with the response of the gas sensor as the flow of analyte is introduced/withdrawn is expected to be within the range from about few tens of seconds to about few hundreds of seconds.

In one embodiment, the gas sensor may be used to monitor and/or measure the concentration of at least one analyte in the exhaust of an internal combustion engine. For instance, the gas sensor may be positioned for optimal monitoring and/or measurement of at least one analyte within the exhaust system of an automobile. In another embodiment, a plurality of gas sensors may be positioned at different locations within the exhaust system of the automobile to monitor and measure the concentration of analytes in the exhaust. In another embodiment, the gas sensor may be used to monitor and/or measure the concentration of at least one analyte at any locations within the automobile. For instance, one or more gas sensors may be positioned for optimal monitoring and/or measurement of at least one analyte within an automobile interior.

Embodiments of the gas sensor of the present invention may also be used to monitor emission of $NO_x$ in applications including, but not limited to, aluminum, cement, fertilizer, glass, mineral wool, power, steel, sulphuric acid, and waste incineration industries. In the automobile sector, embodiments of the gas sensor may be used to monitor emissions in a variety of applications including, but not limited to, the emission of $NO_x$ from petrol, gasoline, diesel engine, internal combustion engine, automobiles including, but not limited to, passenger cars, light commercial vehicles, lorries, trucks, and buses.

The gas sensor may also be used to meet the U.S. Environmental Protection Agency continuous emissions monitoring standards (CEMS) outlined in 40 C.F.R. §60 and 40 C.F.R. §75. The gas sensor may further be used to meet the European Union CEN emissions limit values. Still further, the gas sensors may be used in a continuous emissions monitoring system to determine "cap and trade" allowances as described by local and federal regulating authorities.

In another aspect, a gas sensor is arranged within an encapsulation in a flip-chip arrangement. In a flip-chip arrangement, the gas sensor is flipped upside down, such that all of the top sensitive surface area of the device including the area surrounding the sensitive areas of the device, are protected from gases to be monitored. An additional protective board protects the back surface of the chip. Directly over the sensitive area of the device, a slit, or opening in the ceramic board to which the chip's top surface is mounted, is created to allow the gases to flow to the gas sensing layer. A layer of high temperature stable conductive material, such as Pt or Au, may be used to interconnect the components of the gas sensor to leads in the encapsulation layer. This flip chip arrangement enables interconnect in a higher vibration and higher temperature, for example greater than 500° C., environments than conventional wire bonds, which are susceptible to fatigue failure. The interconnection using platinum and/or gold "bumps" to connect the components, such as the at least one of the electrodes to the leads helps to enable the use of the gas sensor in harsh environments.

In one embodiment the gas sensor may be configured to be operable in harsh environments in which are locations present where a temperature is between about 200° C. and about 800° C. In another embodiment, the gas sensor may be configured to be operable in harsh environments in which locations are present with a temperature between about 200° C. and about 600° C. In yet another embodiment, the gas sensor may be configured to be operable in harsh environments in which are locations are present with a temperature between about 300° C. and about 550° C.

Embodiments of the gas sensor are cost effective in that it has a long working life (on the order of about 1000 hours) and provides highly repeatable readout. The cost effectiveness is further enhanced because of the simple modular design of these sensors allowing ready scaling of the manufacturing process to large volumes.

The gas sensor may be encapsulated in a packaging. The encapsulation further protects the gas sensor from the high temperature and corrosive atmosphere in the harsh environments where these sensors are likely to be used. The encapsulation acts to cover exposed surfaces of such elements of the device as the adhesion layer, the electrodes, the first glass layer, the thermometer, the second glass layer, the heater, and the substrate, which do not by themselves, sense the gases. This encapsulation also may involve forming a bond with the underlying layer (substrate), so as to inhibit flow of gases and corrosive materials (e.g., particulate matter, hydrocarbons) that would be detrimental to the gas sensor over time. Examples of such suitable materials for encapsulation include, but are not limited to, silicon carbide, ceramic-based epoxies such as those containing alumina, glass, quartz, silicon nitride, silicon dioxide and a combination thereof.

The encapsulation layer can be deposited by any known method, such as plasma enhanced chemical vapor deposition (PECVD), low-pressure chemical vapor deposition (LPCVD), and a combination thereof. The encapsulation is such that at least a portion of the gas sensing layer remains exposed to ambient gases. With the application of an encapsulation the sensors may be protected in harsh environments and have a longer working life. Such protection against harsh environments would allow for the use of these sensors in a wide variety on settings, including but not limited to, boiling water reactor, automotive and locomotive petrol or diesel engine exhaust, industrial process (glass, aluminum, steel, and petroleum) plant exhaust. It would further protect the gas sensor from the particulate matter that may be present in the exhaust streams of the previously mentioned environments. Such particulate matter may potentially be detriment to the gas sensor as they may adhere to and/or corrode the gas sensor thereby hindering the detection of exhaust gases by hindering contact between the exhaust gases and the gas sensor.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A gas sensor comprising:
    a gas sensing layer comprising at least one metal oxide compound and at least two dopant species, the said gas sensing layer being capable of detecting at least one analyte selected from the list comprising NO, $NO_2$, $NH_3$, $H_2O$, and combinations thereof, in harsh environments;
    at least one electrode in communication with the said gas sensing layer;
    an adhesion layer, comprising a chemical element selected from the group consisting of Ti, Cr, and combinations thereof; and
    a response modification layer, consisting of at least one chemical element selected from the group consisting of Ti, Re, Ni, Ta, Nb, Mo, Zr, and combinations thereof, adjacent to the gas sensing layer and the adhesion layer;
    wherein said metal oxide is selected from the list of metal oxides consisting of W, Ta, and Nb; and
    wherein said dopant species are selected from the list of chemical elements consisting of Re, Ni, V, Ta, Nb, Mo, and Zr.

2. The gas sensor of claim 1, wherein the said at least one electrode is positioned within the adhesion layer.

* * * * *